United States Patent
Takasawa (12)

(10) Patent No.: US 6,542,579 B1
(45) Date of Patent: Apr. 1, 2003

(54) X-RAY PHOTO-TAKING SYSTEM, X-RAY PHOTO-TAKEN IMAGE DISPLAY METHOD, AND STORAGE MEDIUM

(75) Inventor: Toru Takasawa, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/404,837

(22) Filed: Sep. 24, 1999

(30) Foreign Application Priority Data

Sep. 30, 1998 (JP) ............................................. 10-291386

(51) Int. Cl.⁷ ................................................. G21K 4/00
(52) U.S. Cl. ........................................ 378/165; 378/162
(58) Field of Search ................................ 378/165, 162, 378/8, 4

(56) References Cited

U.S. PATENT DOCUMENTS

| | | | | |
|---|---|---|---|---|
| 4,739,480 A | * | 4/1988 | Oono et al. | 364/414 |
| 5,371,778 A | * | 12/1994 | Yanof et al. | 378/901 |
| 5,694,450 A | * | 12/1997 | Livingston | 378/166 |
| 5,986,662 A | * | 11/1999 | Argiro et al. | 345/424 |
| 6,055,326 A | * | 4/2000 | Chang et al. | 382/132 |

FOREIGN PATENT DOCUMENTS

| | | |
|---|---|---|
| JP | 56-083731 | 7/1981 |
| JP | 59-028145 | 2/1984 |

* cited by examiner

*Primary Examiner*—Robert H. Kim
*Assistant Examiner*—Hoon K. Song

(57) ABSTRACT

This invention provides an X-ray photo-taking system, X-ray photo-taken image display method, and storage medium by which an operator can readily understand the position (right, left, or center) of a photo-taking region of an object to be examined, the X-ray irradiation direction, and the photo-taking attitude only by monitoring an X-ray image, and by which text information is narrowed down to patient information and photo-taking information to make these pieces of information easy to see. The system includes an information capture portion for symbolizing the direction of an object to be examined during photo-taking, the photo-taking direction, the position of a photo-taking region, and the photo-taking attitude, a mark embedding portion for embedding a mark in a portion of an image, a display control portion for displaying the X-ray photo-taken image in which the mark is embedded by the mark embedding portion, and a transmission portion for transmitting the X-ray photo-taken image in which the mark is embedded by the mark embedding portion to a network.

45 Claims, 12 Drawing Sheets

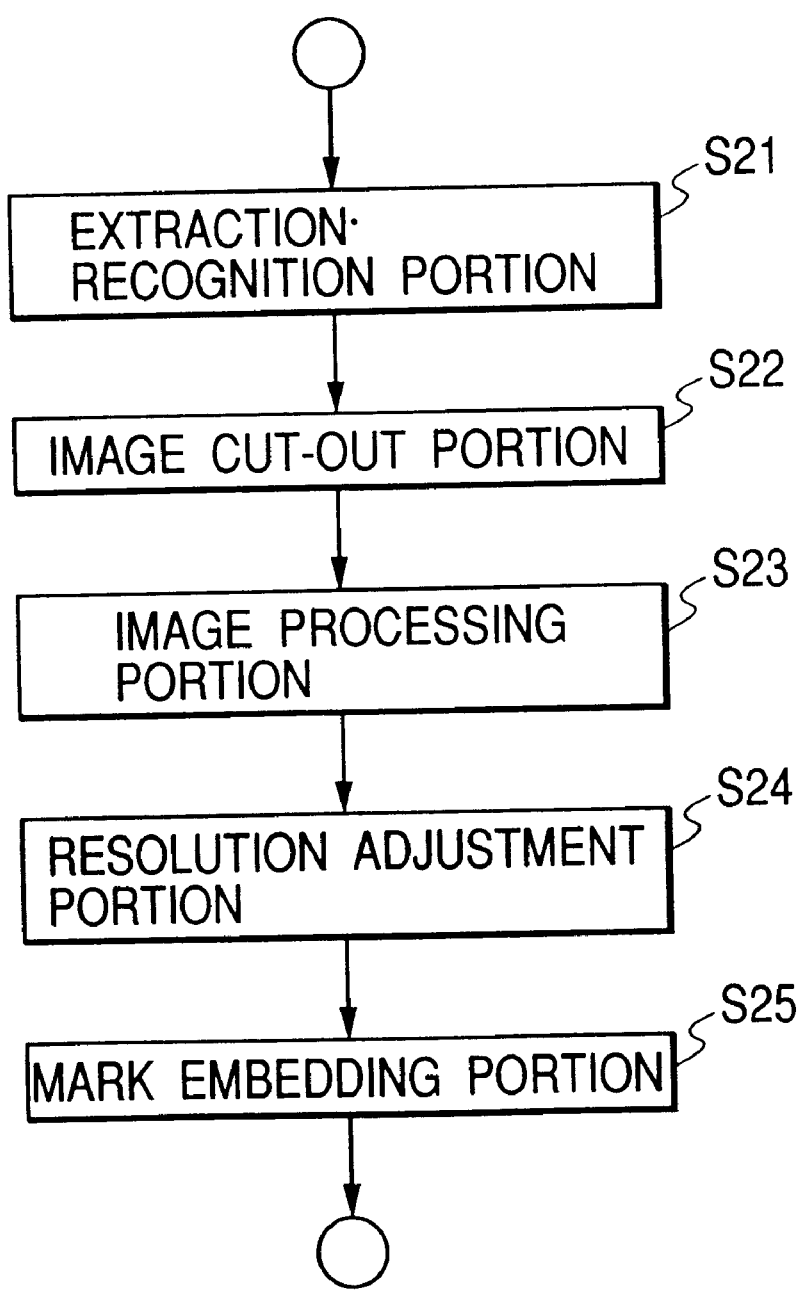

AN EXAMPLE OF LEFT SHOULDER JOINT
(BACK→FRONT AXIAL LIGATION)
PHOTO-TAKING

AN EXAMPLE OF THORACIC PART
(BACK→FRONT) PHOTO-TAKING

FIG. 10

| PHOTO-TAKING REGION | MARK COMBINATION (IN RANDOM ORDER) | | | | FORMAT | |
|---|---|---|---|---|---|---|
| THORACIC PART | P→A | R→L | | | (LEFT) R→L (RIGHT) P→A | |
| | P→A | L→R | | | (LEFT) P→A (RIGHT) L→R | |
| | A→P | R→L | | | (LEFT) R→L (RIGHT) A→P | |
| | A→P | L→R | | | (LEFT) A→P (RIGHT) L→R | |
| | A→P, R | A→P, L | | | (LEFT) A→P, L (RIGHT) A→P, R | |
| | A→P, R | Lat, R | | | (LEFT) Lat, R (RIGHT) A→P, R | |
| | A→P, R | Lat, R | Lat, L | | (LEFT) Lat, R (RIGHT) A→P, R | (LEFT) A→P, L (RIGHT) Lat, L |
| | ...... | | | | ...... | |
| WRIST JOINT | ............ | | | | | |

AN EXAMPLE OF THORACIC PART
(BACK→FRONT) PHOTO-TAKING

AN EXAMPLE OF LEFT SHOULDER JOINT (BACK→FRONT AXIAL LIGATION) PHOTO-TAKING

AN EXAMPLE OF THORACIC PART (BACK→FRONT) PHOTO-TAKING

X-RAY PHOTO-TAKING SYSTEM, X-RAY PHOTO-TAKEN IMAGE DISPLAY METHOD, AND STORAGE MEDIUM

BACKGROUND OF THE INVENTION

1. Field of the Invention

The present invention relates to an X-ray photo-taking system, X-ray photo-taken image display method, and storage medium for obtaining an X-ray transmission image of an object to be examined and, more particularly, to an X-ray photo-taking system, X-ray photo-taken image display method, and storage medium suited to display an X-ray photo-taken image after photo-taking.

2. Related Background Art

Conventionally, an X-ray photographing system combining an intensifying screen and a film in an X-ray detection portion has been extensively used as an X-ray photo-taking apparatus for medical diagnostic purposes. In this system, when X-rays transmitted through an object to be examined enter the intensifying screen, a phosphor contained in this intensifying screen absorbs the X-ray energy to emit fluorescence. This fluorescence exposes the X-ray film to form a radiation image as a latent image on the film. This X-ray image is visualized by developing and fixing the film.

To allow easy image reading by a doctor at a later time, not only the X-ray transmission image of the object but also the corresponding patient information, photo-taking direction, and the like are simultaneously imprinted on the film. If a lesion is present in a portion where regions overlap each other, it is not easy to identify the lesion in many instances. If this is the case, judgement is made statistically by taking account of the photo-taking conditions and the age and sex of the patient. Also, in photo-taking of a thoracic (hereinafter, also referred to as "chest") part, many doctors customarily perform image reading by placing an X-ray film in Schaukasten (a film viewing box; a flim viewer) such that the heart of a patient is on the right-hand side of an image. When photo-taking is performed by irradiating an object to be examined with X-rays from behind, the heart is positioned on the left-hand side on a film, so the image must be displayed by reversing it from right to left.

Accordingly, as shown in FIG. 12A, patient information is imprinted as it is laterally inverted, and at the same time a mark (P→A) indicating the photo-taking direction is printed. When the film is turned over, the mark is reversed from right to left and displayed in the laterally opposite position. Therefore, a doctor can recognize the irradiation direction of X-rays at a glance and can immediately understand the original direction. Furthermore, right and left shoulder joints, wrist joints, and limbs are separately photo-taken, so the side (right or left) and the direction are difficult to distinguish with no marks. That is, an image obtained by irradiating a right shoulder joint with X-rays from the front and an image obtained by photo-taking a left shoulder joint from behind have almost equal outer shapes. This is also true of wrist joints, ankle joints, forearms, upper arms, thighbones, and lower leg bones.

For this reason, marks (P→A and L) as shown in FIG. 12B are printed on a film. These marks are formed by attaching an X-ray shielding member to an irradiation area and masking X-rays during X-ray irradiation or by optical irradiation to an X-ray through area, where no object image exists, on an X-ray film. The latter method generally uses an LCD or LED as a light source. One prior art is an apparatus for projecting a data image onto a film as described in Japanese Patent Application Laid-Open No. 56-83731.

Recently, various methods of digitally detecting and generating X-ray images have been developed. One representative method is an X-ray image acquisition method using a flat sensor panel. This method uses a unit combining a solid-state image sensor which is sensitive to X-rays and outputs an electrical signal corresponding to the detected X-ray intensity by converting the detected X-rays, or a phosphor which absorbs the energy of X-rays and emits fluorescence having intensity corresponding to the energy, and an photoelectric conversion element which is sensitive to visible light and converts visible light into an electrical signal corresponding to the intensity of the light. Analog signals from these devices are A/D-converted and input as digital signals.

This digital X-ray photo-taking apparatus comprises a sensor unit for detecting an electrical amount corresponding to an X-ray transmission dose and converting the detected electrical amount into a digital amount, and a controller for this sensor unit. An X-ray photo-taking system is often constructed by combining this digital X-ray photo-taking apparatus with a monitor or printer, for displaying or printing photo-taken images, and an X-ray generator. In this digital X-ray photo-taking system, the sensor unit supplies digital image data to the controller where various image processing operations are performed to form an X-ray image. FIG. 13 shows an example of conventional chast part (back→front) photo-taking.

Image reading by a doctor requires object information such as the ID, name, sex, and age, photo-taking information such as the photo-taking direction, the photo-taking method, and the position of a region, and some image processing parameters. Therefore, to display an X-ray image and some of these data on a film or a monitor, the X-ray image is displayed in an upper portion, and text information such as the object information and the photo-taking information are described below this X-ray image. A doctor interprets this X-ray image. When a display medium of the X-ray image is a film, this film is placed in a film viewing box and interpreted. In this case, a doctor places the film by laterally inverting it so that the heart is seen on the right-hand side. When image reading is performed following this procedure, inverting each film is cumbersome if a large number of films are to be interpreted.

To solve this problem, a radiation image reproducing apparatus is disclosed in Japanese Patent Application Laid-Open No. 59-28145. In this apparatus, if it is determined by referring to the photo-taking direction that a radiation image is photo-taken in an opposite direction to a common observation direction of an object to be examined, the image is laterally inverted and printed on a film. In this case, however, although the film need not be inverted, the photo-taking direction and the photo-taking method cannot be immediately identified in comparison to films photo-taken by the X-ray photographing system. Also, in monitor diagnoses, it is necessary to laterally invert images after photo-taking. Additionally, when the laterally inverted images are again stored, the direction of X-ray irradiation cannot be immediately determined.

Furthermore, when symmetrical regions such as "shoulder joints", "wrist joints", "ankle joints". "forearms", "upper arms", "thighbones", and "lower leg bones" are photo-taken in different directions, it is not easy to display the images in appropriate layout and readily understandable form.

In the prior art as described above, object information and photo-taking parameters are displayed at the same time an X-ray photo-taken image is displayed. However, it is difficult to distinguish between the right and the left and recognize the irradiation direction with only text data. Additionally, when an image is inverted, the direction of an original image cannot be known. When right and left regions are photo-taken, on which side each image is taken cannot be readily understood. Furthermore, images of the same region but in different directions cannot be displayed on the same medium with simple operation.

The present invention has been made in consideration of the above situation, and has as its first object to provide an X-ray photo-taking system, X-ray photo-taken image display method, and storage medium by which an operator can readily understand the position (right, left, or center) of a photo-taking region of an object to be examined, the X-ray irradiation direction, and the photo-taking attitude only by monitoring an X-ray image, and by which text information is narrowed down to patient information and photo-taking information to make these pieces of information easy to see.

Also, the present invention has been made in consideration of the above situation, and has as its second object to provide an X-ray photo-taking system, X-ray photo-taken image display method, and storage medium by which when images of the same region but in different photo-taking directions are to be displayed on the same medium, readily understandable formatting can be performed with simple operation.

SUMMARY OF THE INVENTION

One embodiment of the present invention provides an X-ray photo-taking system for acquiring an X-ray photo-taken image by irradiating an object to be examined with X-rays, comprising symbolizing means for symbolizing input information pertaining to X-ray photo-taking of the object, and symbol embedding means for displaying a symbol obtained by the symbolizing means by embedding the symbol in a portion of the X-ray photo-taken image.

BRIEF DESCRIPTION OF THE DRAWINGS

FIG. 5 is a flow chart of image processing and mark embedding portions in the X-ray photo-taking system according to the first embodiment of the present invention;

FIGS. 6A and 6B are views for explaining mark-embedded display examples in the X-ray photo-taking system according to the first embodiment of the present invention, in which FIG. 6A shows an example of chast part (back→front) photo-taking and FIG. 6B shows an example of left shoulder joint (back e front axial ligation) photo-taking;

FIG. 10 is a view for explaining a format table in the X-ray photo-taking system according to the third embodiment of the present invention;

FIGS. 12A and 12B are views for explaining examples of mark printing in an X-ray photographing system according to prior art, in which FIG. 12A shows an example of chast part (back→front) photo-taking and FIG. 12B shows an example of left shoulder joint (back→front axial ligation) photo-taking.

DESCRIPTION OF THE PREFERRED EMBODIMENTS

Embodiments of the present invention will be described below with reference to the accompanying drawings.

FIRST EMBODIMENT

Figure 1:
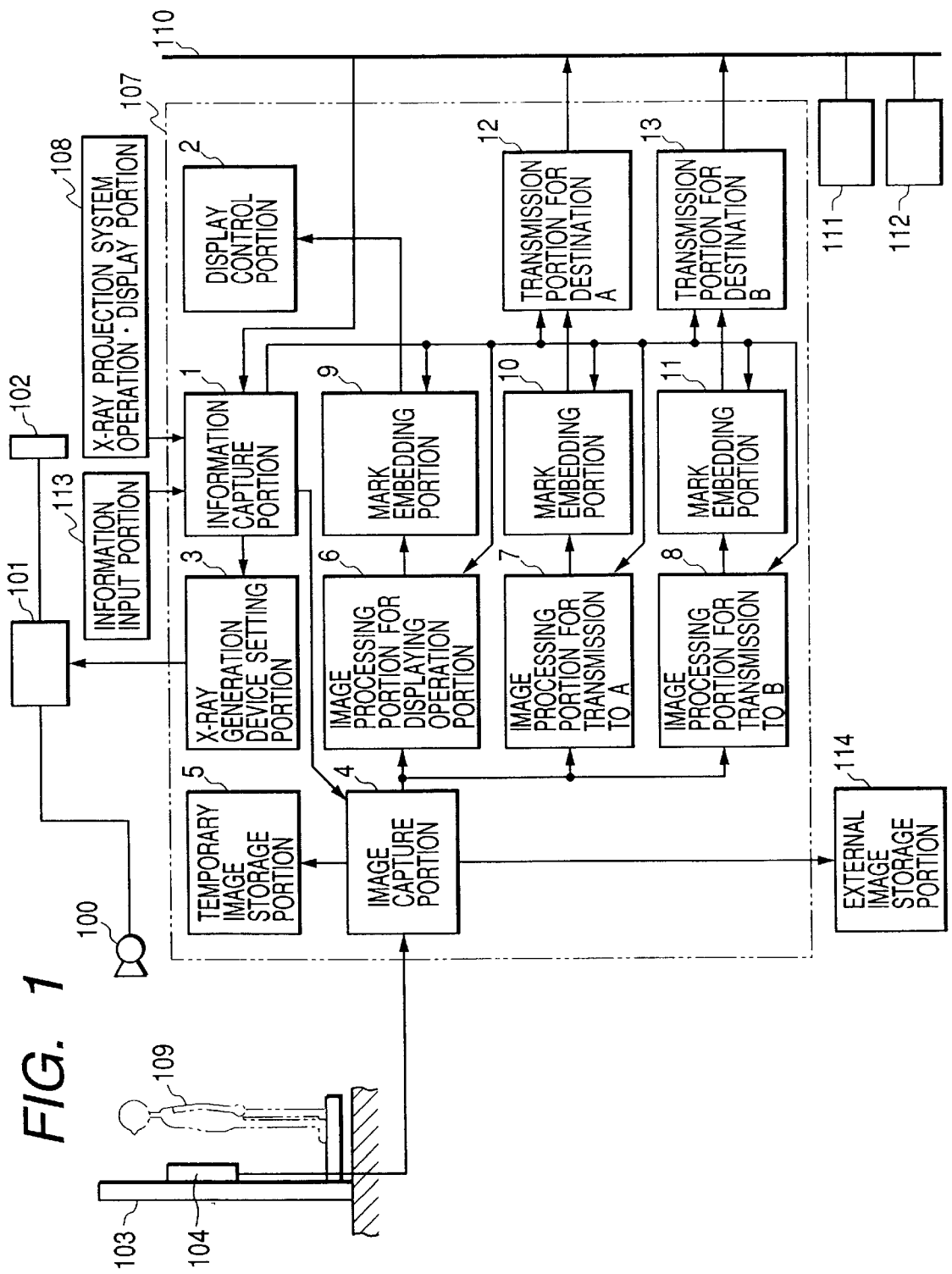
FIG. 1 is a block diagram showing the overall arrangement of an X-ray photo-taking system according to the first and second embodiments of the present invention.

FIG. 1 is a block diagram showing the overall arrangement of an X-ray photo-taking system according to the first embodiment of the present invention.

This X-ray photo-taking system according to the first embodiment of the present invention comprises an X-ray tube 100, an X-ray generation device control portion 101, an X-ray generation device operation.display portion 102, a standing position sensor unit 103, a standing position sensor panel 104, an X-ray photo-taking system control portion 107, an X-ray photo-taking system operation.display portion 108, a network 110, a film imager 111, an image server 112, an information input portion 113, and an external image storage portion 114. The X-ray photo-taking system control portion 107 includes an information capture portion 1, a display control portion 2, an X-ray generation device setting portion 3, an image capture portion 4, a temporary image storage portion 5, an image processing portion 6 for displaying operation portion, an image processing portion 7 for transmission to A, an image processing portion 8 for transmission to B, mark embedding portions 9, 10, and 11, a transmission portion 12 for destination A, and a transmission portion 13 for destination B.

Each of the above components will be described in detail below. The X-ray tube 100 radiates X-rays. The X-ray generation device control portion 101 controls the X-ray generation device. The X-ray generation device operation.display portion 102 is used for operation and display of the X-ray generation device. These components are generally collectively called an X-ray generation device.

An X-ray photo-taking apparatus is constructed of the standing position sensor unit 103 capable of standing position X-ray photo-taking and the X-ray photo-taking system control portion 107 for controlling this standing position sensor unit 103. In this embodiment, the X-ray photo-taking system operation.display portion 108 is composed of, e.g., an LCD (Liquid Crystal Display) and a touch panel sensor. As this LCD, a product having a resolution of 640×480 dots is used because of low cost. The information input portion 113 is constructed as any of various information input devices such as a magnetic card reader or a bar code reader. Object information is input using this information input portion 113. The standing position sensor panel 104 is constructed of a phosphor which absorbs the energy of X-rays and emits fluorescence having intensity corresponding to the absorbed energy, and a photoelectric conversion element which is sensitive to visible light and converts visible light into an electrical signal corresponding to the intensity of the light. After X-ray irradiation, electric charge equivalent to the transmitted X-ray amount is A/D-converted and captured as an electronic image by the X-ray photo-taking system control portion 107. The sensor portion has a size of, e.g., 430×430 mm and a resolution of, e.g., 2,700× 2,700 dots. The network 110 connects the X-ray photo-taking system 107 to the image server 112 and the film imager 111.

The X-ray photo-taking system control portion 107 executes processes shown in the flow charts of FIG. 5 (first embodiment) and FIG. 9 (third embodiment) to be described later. In this X-ray photo-taking system control portion 107, the information capture portion 1 captures object information data and photo-taking region information that are input via the X-ray photo-taking system operation.display portion 108, the information input portion 113, or the network 110. The information capture portion 1 supplies X-ray generation device setting parameters, such as tube voltage, tube current, and exposure time (irradiation time), to the X-ray generation device setting portion 3 and supplies the object information to be linked to an X-ray image to the image capture portion 4. The information capture portion 1 also symbolizes information to be embedded in the image and supplies the symbolized information to the mark embedding portions 9 to 11. Note that object information linked to the X-ray image also contains embedding information.

The display control portion 2 controls display on the X-ray photo-taking system operation.display portion 108. The X-ray generation device setting portion 3 transmits the photo-taking condition data captured by the information capture portion 1 to the X-ray generation device control portion 101. The photo-taking conditions are setting conditions of the X-ray generation device, such as tube voltage, tube current, and exposure time. The image capture portion 4 captures an X-ray photo-taken image supplied from the standing position sensor panel 104 and performs basic corrections such as shading correction and gain correction for the captured image. The image capture portion 4 links this image to information attached as text to the image and supplies the outcome to the image processing portion 6 for displaying operation portion, the image processing portion 7 for transmission to A, the image processing portion 8 for transmission to B, the temporary image storage portion 5, and the external image storage portion 114.

The temporary image storage portion 5 is constructed of, e.g., a RAM having high access speed. The external image storage portion 114 is constructed of, e.g., MO (Magneto Optical), ZIP (a medium of the same magnetic type as a floppy disk, developed by U.S. Iomega Corp.), or CD-R (Compact Disc Recordable). The temporary image storage portion 5 is referred to when image processing is to be reexecuted for a photo-taken image.

When the X-ray photo-taking system operation.display portion 108 inputs a command for changing image processing to the information capture portion 1, a temporary image storage portion image reading portion (not shown) reads out image data from the temporary image storage portion 5. The readout data is again supplied to the image processing portion 6 for displaying operation portion, the image processing portion 7 for transmission to A, and the image processing portion 8 for transmission to B, and the changed image processing is performed. When image processing is to be again changed and transmitted after photo-taking, the X-ray photo-taking system operation.display portion 108 outputs a command for reading out an image. An external image storage portion reading means (not shown) reads out image data from the external image storage portion 114, transmits the readout image data to the temporary image storage portion 5, and transmits to the mark embedding portions 9 to 11 marks to be embedded.

The image processing portion 6 for displaying operation portion, the image processing portion 7 for transmission to A, and the image processing portion 8 for transmission to B perform a cut-out process, a gradation process, a dynamic range compression process, an edge emphasis process, a reduction process, and the like such that a region of interest is clearly seen. The display characteristics such as the γ characteristics of a monitor and the density characteristics of a film change in accordance with a display medium. Also, parameters of the individual processes change in accordance with the resolution of a display medium. Therefore, the X-ray photo-taking system operation.display portion 108, the image processing portion 6 for displaying operation portion, the image processing portion 7 for transmission to A, and the image processing portion 8 for transmission to B perform image processing meeting the display characteristics.

The mark embedding portions 9, 10, and 11 embed marks in the images obtained by the image processing portion 6 for displaying operation portion, the image processing portion 7 for transmission to A, and the image processing portion 8 for transmission to B. These mark embedding portions 9, 10, and 11 transmit an image to be displayed on the X-ray photo-taking system operation.display portion 108 to the display control portion 2, image data to be transmitted to the destination A to the transmission portion 12 for destination A, and image data to be transmitted to the destination B to the transmission portion 13 for destination B. The transmission portion 12 for destination A and the transmission portion 13 for destination B transmit the image data and the attached text data to the destinations.

The correspondence of constituent features in the scope of claims to the individual portions in the X-ray photo-taking systems according to this first embodiment and the second and third embodiments to be described later is as follows.

A symbolizing means corresponds to the information capture portion 1 of the X-ray photo-taking system control portion 107. A symbol embedding means (embedding function) and inversion/non-inversion determining means correspond to the mark embedding portions 9 to 11 of the X-ray photo-taking system control portion 107. A symbol embedding means (display control function) corresponds to the display control portion 2 of the X-ray photo-taking system control portion 107. An information input means corresponds to the X-ray photo-taking system operation.display portion 108, the information input portion 113, and the network 110. A setting control means corresponds to the X-ray generation device setting portion 3 of the X-ray photo-taking system control portion 107. First and second extracting means correspond to an extraction function (step S21 of the flow chart in FIG. 5) of the X-ray photo-taking system control portion 107. A selecting means, relating means, photo-taking region designating means, embedding setting means, and embedding changing means correspond to the X-ray photo-taking system operation.display portion 108. An image formatting means corresponds to image format portions 14 to 16. An image transmitting means corresponds to the transmission portion 12 for destination A, the transmission portion 13 for destination B, and the image capture portion 4. An image output means corresponds to the film imager 111 and the image server 112. An image storage means corresponds to the external image storage portion 114 and the temporary image storage portion 5 of the X-ray photo-taking system control portion 107.

Figure 2:
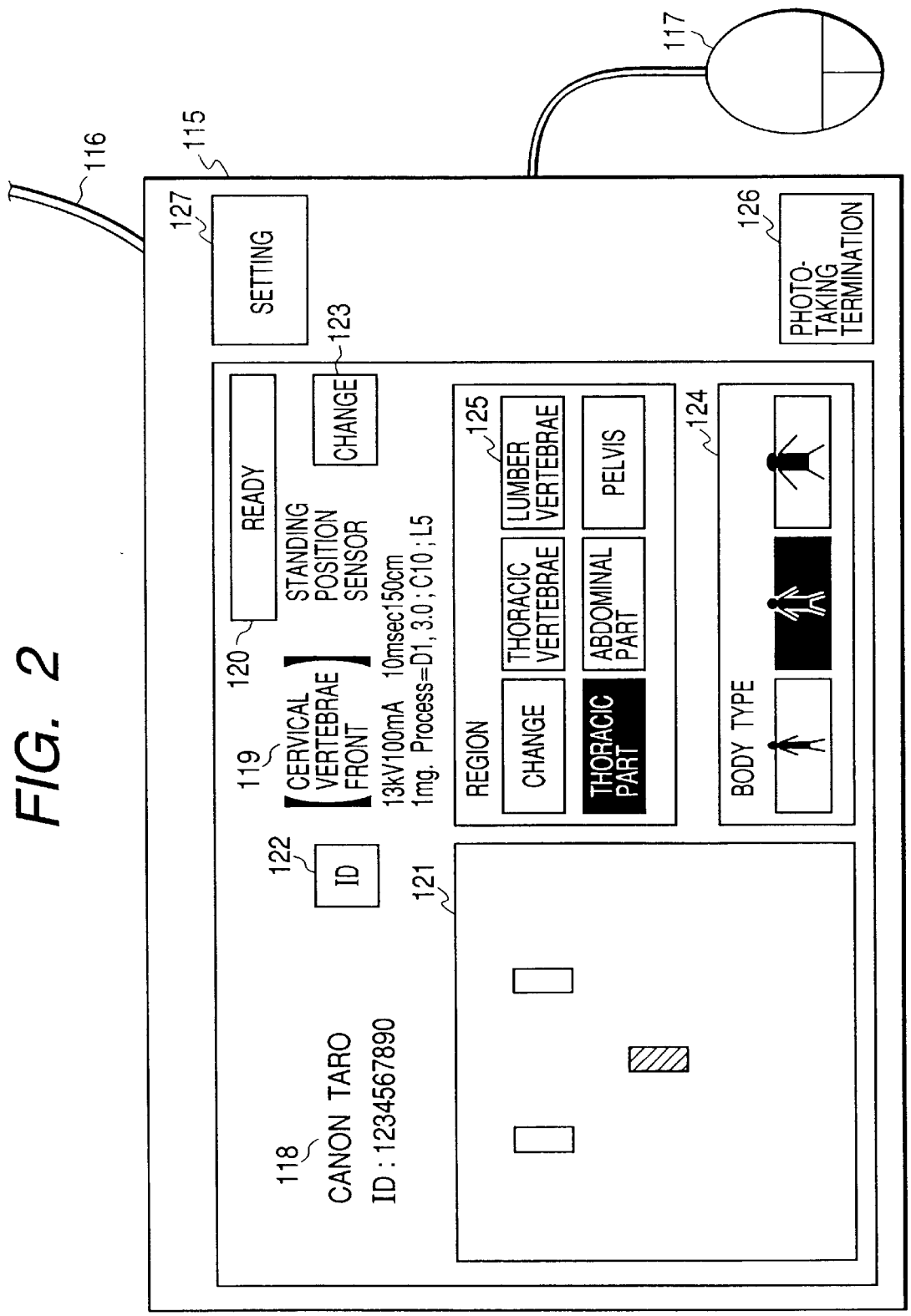
FIG. 2 is a view for explaining an X-ray photo-taking system operation.display portion in the X-ray photo-taking system according to the first embodiment of the present invention.

FIG. 2 is a view for explaining the screen of the X-ray photo-taking system operation.display portion 108 of the X-ray photo-taking system according to the first embodiment of the present invention. An operation.display portion main body 115 shows the state of the system and has keys for operating the system. In this embodiment, this operation.display portion main body 115 is composed of, e.g., an LCD and touch panel sensor. A cable 116 is used to, e.g., communicate with the X-ray photo-taking system control portion 107. This cable 116 is constructed of a UGA cable, a power cable, a serial cable for communication with the touch sensor, and a mouse cable. An operator operates this operation.display portion main body 115 of the X-ray generation device by sending signals from the touch sensor by directly touching the monitor or by using the mouse.

The operation screen includes a message area 120, an image display area 121, an object information display area 118, a photo-taking condition display area 119, and various setting keys. The setting keys are: a patient (object) information dialogue call key 122 for calling a patient information input dialogue; photo-taking region keys 125 for inputting a photo-taking region; body type keys 124 for inputting the body type of a patient; a photo-taking termination key 126 to be pressed when photo-taking for each object to be examined is completed; a photo-taking parameter change key 123 for changing set photo-taking conditions or image processing parameters; and a setting key 127 for performing various settings.

The object information display area 118 displays object information, i.e., displays the name, ID, sex, and date of birth of an object to be examined. The photo-taking condition display area 119 displays photo-taking conditions, i.e., displays a photo-taking region, photo-taking conditions such as tube voltage and tube current, and image processing parameters. The display contents in this area are preset values of parameters pertaining to regions selected by the photo-taking region keys 125.

Figure 3:
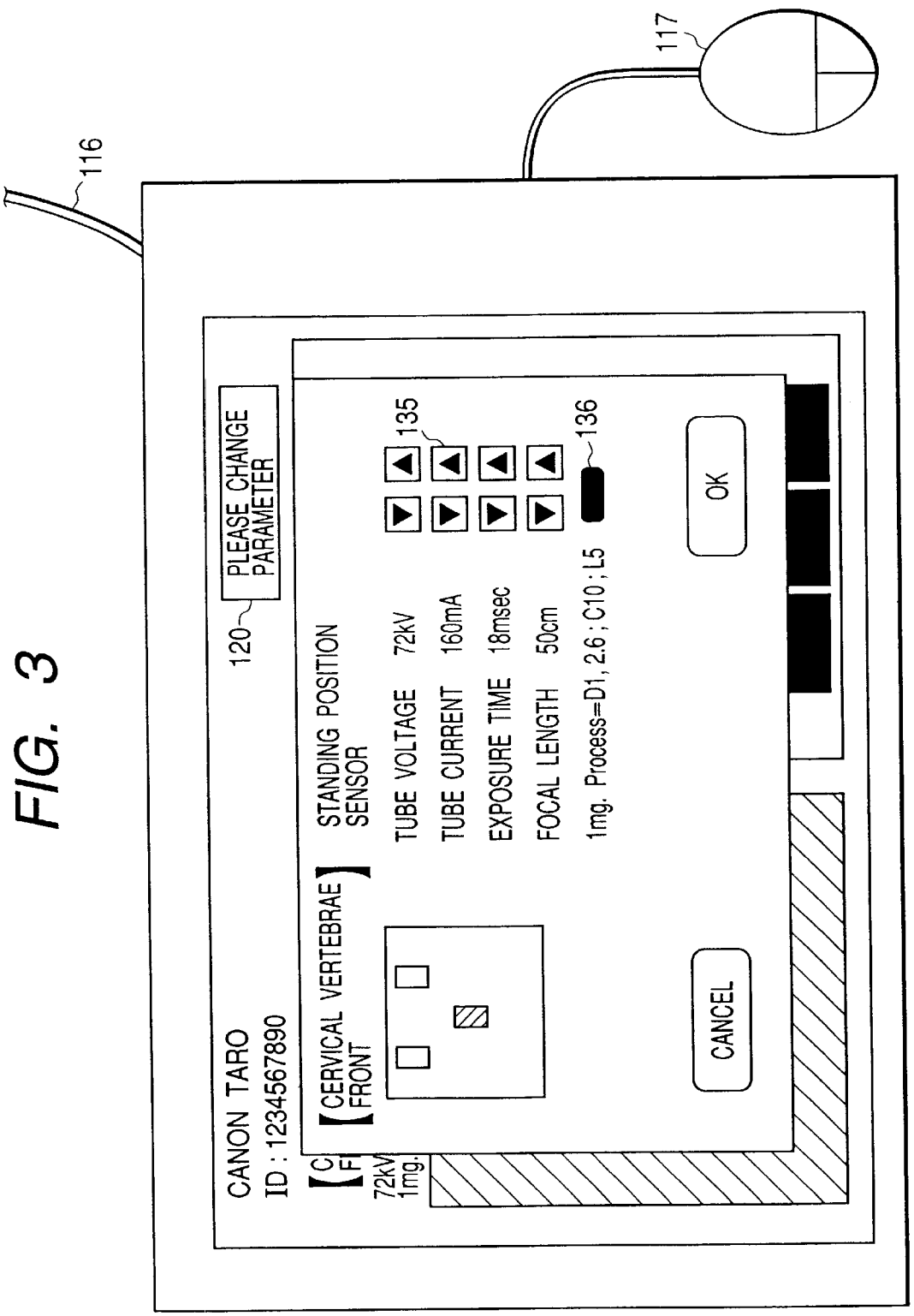
FIG. 3 is a view for explaining a photo-taking condition display portion change dialogue in the X-ray photo-taking system according to the first embodiment of the present invention.

FIG. 3 is a view for explaining a photo-taking condition display portion change dialogue in the X-ray photo-taking system according to the first embodiment of the present invention. To change a parameter, an operator calls and changes the photo-taking condition display portion change dialogue in FIG. 3 by using the photo-taking condition display portion change dialogue call key (photo-taking parameter change key) 123. Referring to FIG. 3, photo-taking condition change keys 135 are up and down keys for changing photo-taking conditions. An image processing parameter change key 136 is pressed by an operator to call the change dialogue and change a parameter.

Figure 4:
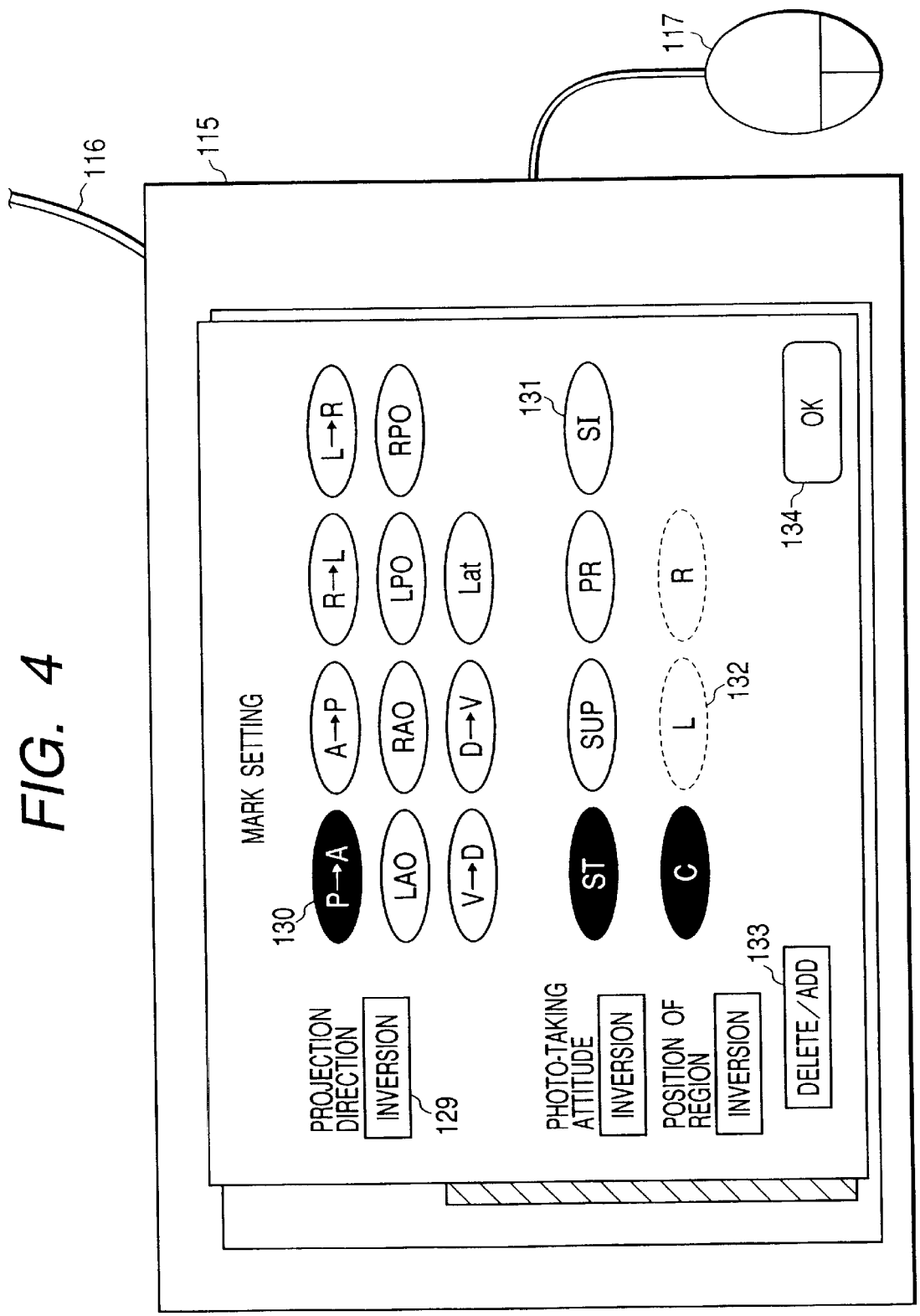
FIG. 4 is a view for explaining a mark setting dialogue in the X-ray photo-taking system according to the first embodiment of the present invention.

FIG. 4 is a view for explaining a mark setting dialogue in the X-ray photo-taking system according to the first embodiment of the present invention. This mark setting dialogue is called after one of the photo-taking region keys 125 is selected. The mark setting dialogue contains: photo-taking direction keys 130 including "P→A" (irradiate from back to front), "V→D" (irradiate from the back to the belly), "A→P" (irradiate from front to back), "D→V" (irradiate from the belly to the back), "LAO" (second back-to-belly oblique position), "RAO" (first back-to-belly oblique position), "LPO" (first belly-to-back oblique position), and "RPO" (second belly-to-back oblique position); photo-taking attitude keys 131 such as "SUP" (lying face up), "PR" (lying face down), and "ST" (standing position); and position-of-region keys 132 including "C" (center), "R" (right), and "L" (left).

A user can freely delete/add these keys by calling a mark edit screen by pressing a delete/add key 133. Also, changeable setting items change in accordance with a photo-taking region. More specifically, in photo-taking of a limb such as a wrist joint, "center" disappears from the position-of-region keys. Each time an inversion/non-inversion key 129 is pressed, "inversion" and "non-inversion" are switched in a toggle manner. When "inversion" is chosen and an image is displayed as it is inverted liked chast part P A, it is possible to set whether symbols are also inverted together with the image or are displayed in non-inversion state. A setting determination key 134 determines settings.

FIG. 5 is a flow chart of image processing and mark embedding portions in the X-ray photo-taking system according to the first embodiment of the present invention. This flow chart is executed by the-X-ray photo-taking system control portion 107. In step S21, an extraction.recognition portion extracts an irradiation field, an X-ray through portion, and a photo-taking region from a corrected image. In step S22, an image cut-out portion cuts out a photo-taken image from an X-ray image area of, e.g., 430×430 mm on the basis of data of the irradiation field extracted in step S21 by the extraction.recognition portion. The extracted irradiation field data, X-ray through portion, and photo-taking region are temporarily stored.

In step S23, an image processing portion performs a gradation conversion process, a dynamic range compression process, an edge emphasis process, and the like for the image cut out in step S22. In step S24, a resolution adjustment portion adjusts the number of pixels of the image cut out in step S22 and the number of display pixels of a display medium. That is, if the display medium has a higher resolution, the resolution adjustment portion interpolates the data; if the display medium has a lower resolution, the resolution adjustment portion interpolates or thins the data. The criterion of the cut-out portion is that, for example, the size of printer output is equal to the size on the sensor surface. In step S25, a mark embedding portion embeds a mark in the through portion obtained in step S21 by the extraction.recognition portion. Details of this flow chart will be described later.

Figure 6B:
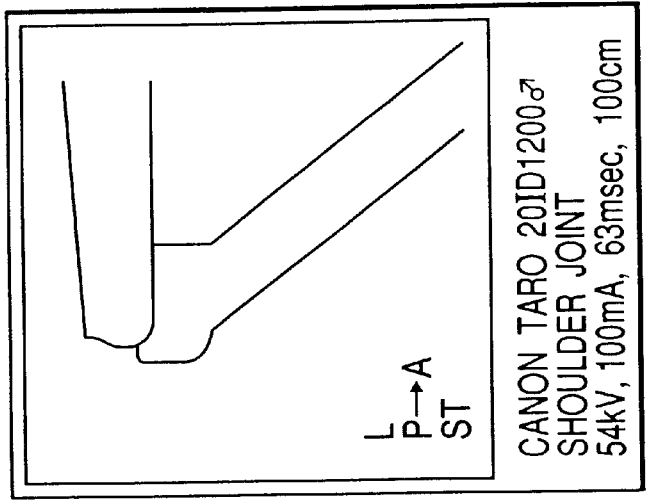
Figure 6A:
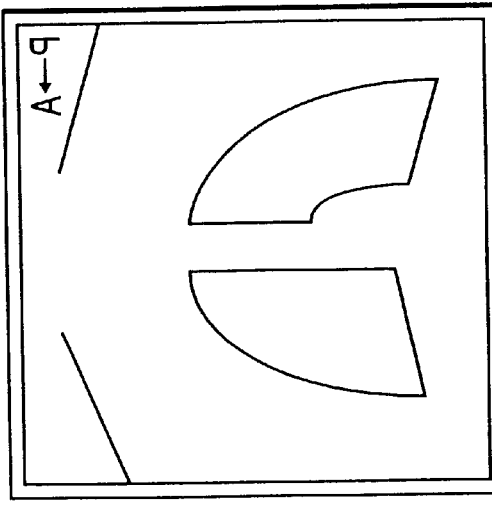

FIGS. 6A and 6B are views for explaining mark-embedded display examples in the X-ray photo-taking system according to the first embodiment of the present invention. FIG. 6A shows an example of thoracic part (back→front) photo-taking. FIG. 6B shows left shoulder joint (back→front axial ligation) photo-taking.

The operation of the X-ray photo-taking system according to the first embodiment of the present invention constructed as above will be described below with reference to FIGS. 1 to 6.

Usually, when finishing out-patient reception, an out-patient goes to the department of corresponding diagnosis (e.g., the department of cerebral surgery, the internal department, the department of surgery, or the department of orthopedic surgery) and is diagnosed. For example, a patient planned to be subjected to thoracic part photo-taking first goes to the internal department and is diagnosed there, and is instructed by the doctor to go to thoracic part X-ray photo-taking. The doctor describes, on an irradiation recording card, a request for X-ray photo-taking of a chast part front or of a chast part front and a thoracic part side. Whether photo-taking of one or both of a thoracic part front and a thoracic part side is to be performed depends on the private opinion of the doctor who requests the photo-taking or is determined in each hospital. The patient goes to the department of radiology with this card and presents the card to the reception. When his or her turn comes, the patient is guided to an examination room in which the X-ray examination system shown in FIG. 1 is installed.

A radiologist in the examination room in which the X-ray examination system shown in FIG. 1 is installed sees the irradiation recording card on which object information such as the name and ID of the patient and the photo-taking request are written. The radiologist calls the patient and conforms these pieces of information. After that, the radiologist inputs these pieces of information by using the X-ray photo-taking system operation.display portion 108. The radiologist inputs the object information, e.g., the name, ID number, date of birth, and sex by pressing the object information input dialogue call key 122. Alternatively, to increase the efficiency of input work and prevent input errors, it is recently also possible to employ a method which causes the information input portion 113 to read a magnetic card, a bar code input method, an input method using the network 110 linked to a hospital information system called HIS, or an input method combining the information input portion 113 and the network 110.

The radiologist also presses the photo-taking region key 125 to set photo-taking conditions such as tube voltage, tube current, exposure time, irradiation field, and grid velocity, and to set image processing parameters. When the photo-taking region key 125 is pressed, the mark setting dialogue as shown in FIG. 4 appears. In this mark setting dialogue, the radiologist inputs the photo-taking direction, the photo-taking method, the photo-taking attitude, and the side on which the region is present.

As the photo-taking direction keys 130, "P→A" (irradiate from back to front), "V→D" (irradiate from the back to the belly), "A→P" (irradiate from front to back), "D→V" (irradiate from the belly to the back), "R→L" (irradiate from the right to the left), "L→R" (irradiate from the left to the right), "LAO" (second back-to-belly oblique position), "RAO" (first back- to-belly oblique position), "LPO" (first belly-to-back oblique position), and "RPO" (second belly-to-back oblique position) are previously registered. As the photo-taking attitude keys 131, "SUP" (lying face up), "PR" (lying face down), and "ST" (standing position) are previously registered. As the position-of-region keys 132, "R" (right) and "L" (left) are previously registered.

In the case of "right shoulder joint front", the operator selects "A→P" by the photo-taking direction key 130 and "standing position" by the photo-taking attitude key 131. Since a chast part is not separated into right and left portions, "center" is always selected by the position-of-region key 132. The operator determines the settings by pressing the setting determination key 134. To change the body type of the object, the operator presses the body type key 124.

The X-ray photo-taking system operation•display portion 108 shown in FIG. 1 transmits the input patient information, photo-taking region information, photo-taking direction information, photo-taking attitude information, photo-taking region position information, and object body type information to the information capture portion 1. In accordance with the combination of the patient information, photo-taking region information, photo-taking direction information, photo-taking attitude information, photo-taking region position information, and object body type information, the information capture portion 1 transmits the preset photo-taking conditions such as tube voltage, tube current, and exposure time to the X-ray generation device setting portion 3, information linked to an image to the image capture portion 4, image processing parameters to the image processing portions 6 to 8, embedding data to the embedding portions 9 to 11, and destination information indicating, e.g., the IP address and port number of the destination to the transmission portions 12 and 13 for destination, thereby enabling photo-taking. Also, the X-ray generation device setting portion 3 transmits the aforementioned photo-taking conditions to the X-ray generation device control portion 101.

The radiologist confirms the pieces of input information on the screen shown in FIG. 2 and adjusts the posture of the object. After the adjustment, the radiologist irradiates the object with X-rays to perform photo-taking. That is, when the radiologist presses an irradiation switch near the X-ray generation device operation.display portion 102, the X-ray tube 100 radiates X-rays toward the standing position sensor unit 103. The X-rays radiated from the X-ray tube 100 are transmitted through the patient as an object to be examined, converted into an electrical amount by the standing position sensor panel 104, and amplified by an amplifier. After that, the signal is subjected to signal processing such as A/D conversion and captured as a digital image by the image capture portion 4.

Additionally, variations between the photoelectric conversion elements constructing the sensors of the standing position sensor panel 104 are corrected, changes over time of the sensor elements are corrected, and scattering line correction and grid correction are also performed. After that, the image is linked to the attached object information, image processing parameters, and photo-taking information, transmitted to the temporary image storage portion 5 and the external image storage portion 114, and at the same time transmitted to the image processing portion 6 for displaying operation portion.

The image transmitted to the image processing portion 6 for displaying operation portion is subjected to various image processing activities. FIG. 5 is a flow chart showing the flow of this image processing. In step S21, the input image is supplied to the extraction.recognition portion (image identification-extraction portion) where the image is analyzed to extract the region of interest, the irradiation field, and X-ray through portion. If "thoracic part front" is designated, a region of lungs is extracted. Data of these extracted irradiation field, through area, and region of interest are used in the image cut-out portion, image processing portion, and mark embedding portion.

In step S22, the image cut-out portion cuts out the image into a desired size on the basis of the irradiation field data extracted in step S21 by the extraction.recognition portion (image identification.extraction portion). In step S23, the image processing portion converts the pixel information by a desired density characteristic curve to form an image having a desired gradation. This density curve generally has a linear shape or an S shape. A rough gradation of a desired image can be obtained in accordance with the level of this density characteristic curve on which the region-of-interest data extracted in step S21 by the extraction.recognition portion (image identification.extraction portion), and with the slope of the density characteristic curve. When an objective region is divided into lungs as low-density regions and a mediastinum as a high-density region, as in the case of chast part photo-taking, and it is necessary to diagnose both regions, dynamic range compression is performed, or edge emphasis is performed to emphasize a small lesion.

In step S24, the resolution adjustment portion reduces the image obtained as described above to a size of about 400×400 such that the image is within the range of the X-ray photo-taking system operation.display portion 108. In step S25, the mark embedding portion embeds the preset "P→A" and "standing position" marks in the image. These marks are displayed as a part of the image information in a location, e.g., an upper right area, where the marks do not interfere with diagnosis of the objective region, in accordance with the through area data and irradiation field data extracted in step S21 by the extraction.recognition portion (image identification.extraction portion). An image lateral inversion portion laterally inverts the image so that the heart is displayed on the right-hand side, and transmits the inverted image to the display control portion 2. The X-ray photo-taking system operation.display portion 8 displays the transmitted image.

FIG. 6A shows an example. This image is displayed in the image display area 121 of the X-ray photo-taking system operation.display portion 108. The operator sees the image display area 121 to check whether the image is not blurred, the graininess is on proper level, and the attitude of the object is correct, and also checks whether the contrast and the density are appropriate. After that, the operator presses the photo-taking termination key to terminate the photo-taking.

If the image is blurred, the graininess is low, or the attitude is incorrect, photo-taking is reexecuted. If the contrast or the density is low, image processing is reexecuted. After that, the image processing portion 7 for transmission to A and the image processing portion 8 for transmission to B start operating on background to cause the mark embedding portions 10 and 11, respectively, to embed and laterally invert marks. Then the transmission portion 12 for destination A and the transmission portion 13 for destination B transmit a file containing text information including the patient information, photo-taking information, and image processing parameters and the X-ray transmission image via the network 110.

The destination is the film imager 111, the image server 112, or the like. The doctor who has requested photo-taking performs image reading. Since regardless of whether image reading is performed on the film imager or on the monitor as a terminal of the image server 112 the image is laterally inverted so that the heart is on the right-hand side as shown in FIG. 6A; the doctor need not take the trouble to invert the image. Also, since the photo-taking direction is displayed in the image area, the irradiation direction of X-rays is known at a glance. Furthermore, even when another radiologist laterally inverts the image, the mark is inverted simultaneously with the image, so the direction of photo-taking is known at a look.

Figure 12B:
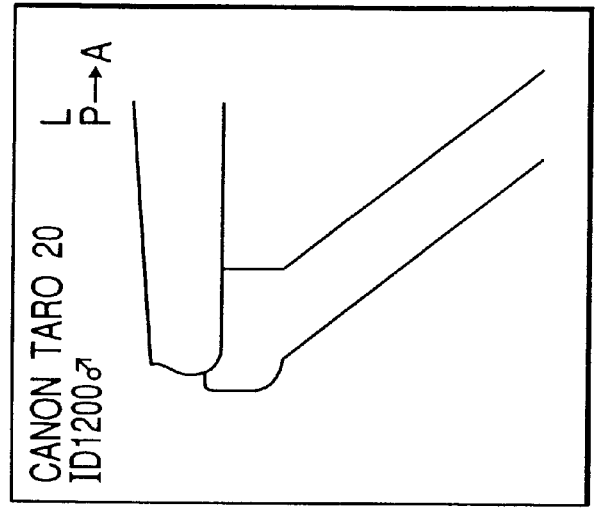
Figure 12A:
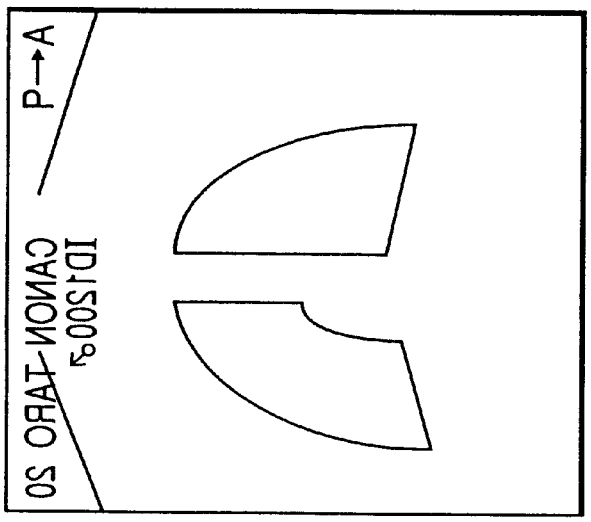

Additionally, the photo-taking direction can be displayed in expression with no sense of incompatibility to doctors or radiologists who have become used to seeing the conventional analog photograph shown in FIG. 12A. In this example, as shown in FIG. 6A, P→A is inverted when displayed during diagnosis. However, in some hospitals, P o A is displayed without being inverted. If this is the case, whether a symbol is to be inverted or not can be set for each item. That is, it is possible to display "P→A" by inverting it and the "standing position" mark without inverting it.

A case where symmetrical regions such as "shoulder joints", "wrist joints", "ankle joints", "forearms". "upper arms", "thighbones", or "lower leg bones" are photo-taken will be described below. In a case like this, a radiologist selects a photo-taking region by the photo-taking region select key 125. At the same time, the radiologist sets the irradiation direction and the photo-taking attitude in the mark setting dialogue and designates the left region or the right region by L or R by using the position-of-region setting key 132. Photo-taking is performed in the same manner as in chast part front. By using the irradiation field data, through area data, and region-of-interest area data extracted in step S21 of FIG. 5 by the extraction.recognition portion (image identification.extraction portion), the mark embedding portion in step S25 embeds a symbol indicating the photo-taking side, the photo-taking direction, and the photo-taking attitude in the X-ray through portion. This mark allows easy recognition of the side on which the region is present and the irradiation direction.

In this first embodiment and the second and third embodiments to be described later, alphabets are used as symbols. However, graphics can also be used because the mark embedding portion directly embeds these symbols in image information.

As described above, the X-ray photo-taking system according to the first embodiment of the present invention comprises the X-ray photo-taking system operation.display portion 108 for inputting and displaying photo-taking conditions, photo-taking parameters, object information, and photo-taking information, the information capture portion 1 for symbolizing the direction of an object to be examined during photo-taking, the photo-taking direction, the position of a photo-taking region, and the photo-taking attitude, the mark embedding portions 9 to 11 for embedding marks in a portion of an X-ray photo-taken image, the display control portion 2 for displaying, on the X-ray photo-taking system operation.display portion 108, an image in which a mark is embedded by the mark embedding portion 9 in an area where no photo-taking object is present within the range of an X-ray irradiation field, and for laterally inverting the image in accordance with the mark, and the transmission portion 12 for destination A and the transmission portion 13 for destination B which transmit an image in which marks are embedded by the mark embedding portions 10 and 11 onto the network 110. Accordingly, the system achieves the following functions and effects.

In the above arrangement, when an operator inputs photo-taking conditions, photo-taking parameters, object information, and photo-taking information via the X-ray photo-taking system operation.display portion 108, the information input portion 113, or the network 110, the mark embedding portions 9 to 11 embed, as marks, the direction of an object to be examined during photo-taking, the photo-taking direction, the position of a photo-taking region, and the photo-taking attitude in a portion of an X-ray photo-taken image. The X-ray photo-taken image in which these marks are embedded is displayed on the X-ray photo-taking system operation.display portion 108 via the display control portion 2. Alternatively, the X-ray photo-taken image in which these marks are embedded is output to the film imager 111 or the image server 112 on the network 110 via the transmission portion 12 for destination A or the transmission portion 13 for destination B. Also, by designating only a photo-taking region, it is possible to set the direction of an object to be examined during photo-taking, the photo-taking direction, the position of a photo-taking region, and the photo-taking attitude, each of which is previously related to the photo-taking region.

Accordingly, by displaying an acquired X-ray phototaken image on a display medium by attaching a mark, indicative of the photo-taking direction or photo-taking method, the photo-taking attitude of an object to be examined, or the position of a photo-taking region of the object, to a portion of the X-ray image, an operator can recognize the position (left, right, or center) of the photo-taking region of the object, the X-ray irradiation direction, or the photo-taking attitude only by seeing the X-ray image.

Additionally, pieces of information pertaining to the position of a photo-taking region of an object to be examined, X-ray irradiation direction, and photo-taking attitude are conventionally displayed in the form of a text in the same space as for photo-taking information and patient information. This makes the text display portion difficult to see. However, in the present invention, these pieces of information are easy to see because the text information can be narrowed down to the patient information and the photo-taking information.

Furthermore, an image is laterally inverted such that the heart is positioned on the right-hand side, so a doctor need not take the trouble to invert the image. Since the photo-taking direction is displayed in an image area, the irradiation direction of X-rays is known at a glance. Even when a radiologist laterally inverts an image, marks are inverted simultaneously with the image, so the direction of photo-taking is known at a look.

Furthermore, whether a symbol is to be inverted or not can be set for each item. Hence, it is possible to display the photo-taking direction (e.g., "P→A") by inverting it and display the photo-taking attitude mark (e.g., "standing position") without inverting it.

SECOND EMBODIMENT

As in the above first embodiment, an X-ray photo-taking system according to the second embodiment of the present invention comprises an X-ray tube 100, an X-ray generation device control portion 101, an X-ray generation device operation.display portion 102, a standing position sensor unit 103, a standing position sensor panel 104, an X-ray photo-taking system control portion 107, an X-ray photo-taking system operation.display portion 108, a network 110, a film imager 111, an image server 112, an information input portion 113, and an external image storage portion 114. The X-ray photo-taking system control portion 107 includes an information capture portion 1, a display control portion 2, an X-ray generation device setting portion 3, an image capture portion 4, a temporary image storage portion 5, an image processing portion 6 for displaying operation portion, an image processing portion 7 for transmission to A, an image processing portion 8 for transmission to B, mark embedding portions 9, 10, and 11, a transmission portion 12 for destination A, and a transmission portion 13 for destination B (FIG. 1). The configurations of the individual portions are described in detail in the above first embodiment, so a detailed description thereof will be omitted.

In this second embodiment of the present invention, the system additionally has a means capable of free layout of the position of marking. In the first embodiment described above, a portion to be marked is determined on the basis of the irradiation field data and the through area data in the extraction.recognition portion (image identification-extraction portion) in step S21 of FIG. 5. In the second embodiment of the present invention, a mark is embedded in a position previously determined for each photo-taking region or photo-taking method. This method has the advantage that neither a portion easy to see nor a through portion need be extracted because marking is done in a predetermined position.

Figure 7:
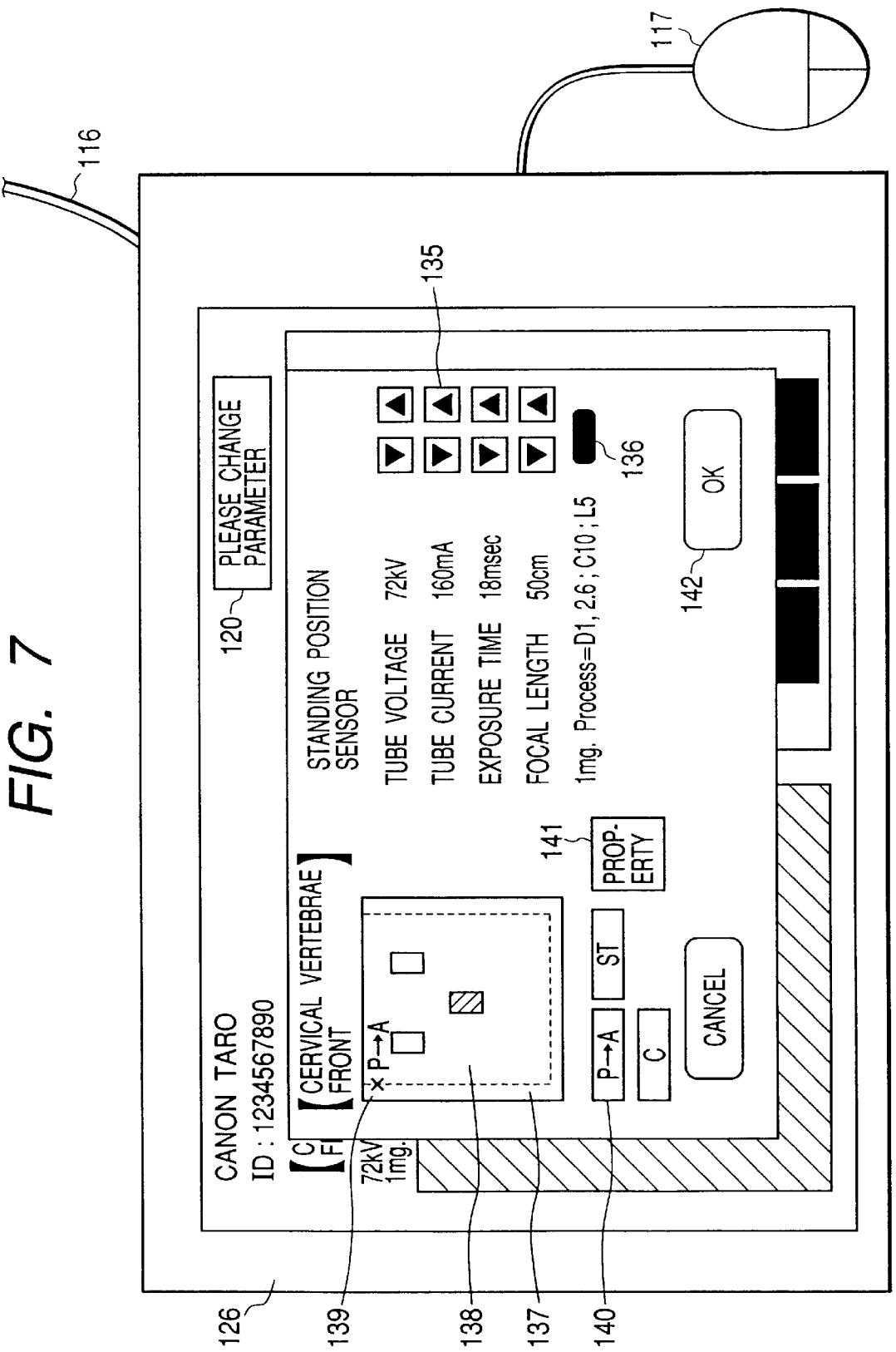
FIG. 7 is a view for explaining a screen which allows editing of a marking position in the X-ray photo-taking system according to the second embodiment of the present invention.

FIG. 7 is a view for explaining a screen capable of editing the position of marking in the X-ray photo-taking system according to the second embodiment of the present invention. In this screen, functions are added to the photo-taking condition display portion change dialogue shown in FIG. 3 in the first embodiment. This dialogue is called in the same way as in the first embodiment. An image cut-out frame 138 is determined by the size of a film of a printer as a destination. Mark layout keys 140 are pressed after the type of a mark to be displayed is chosen from "photo-taking direction", "position of region", and "photo-taking attitude". Consequently, a mark position setting mode is set, and a cursor 139 appears. When the operator moves the cursor to a desired position by touching it and again presses the mark layout keys 140, this position is determined. When the operator presses a property key 141 while pressing the mark layout keys 140, it is possible to change the size of the mark, the type of font if font is used, or the shape of a bitmap if a bitmap is used.

The flow of image processing in the second embodiment of the present invention is shown in FIG. 5 as in the aforementioned first embodiment. The flow is the same as in the first embodiment except that no X-ray through area is extracted in step S21 by the extraction.recognition portion.

Next, the operation of the X-ray photo-taking system according to the second embodiment of the present invention constructed as above will be described below.

Data of an object to be examined is input and photo-taking conditions and image processing parameters are set in the same manner as in the first-embodiment. The posture of the object is adjusted and photo-taking is performed by pressing an irradiation switch as in the first embodiment. Also, image correction after image acquisition and processes in an extraction.recognition (image identification.extraction portion), an image cut-out portion, and an image processing portion are performed in the same way as in the first embodiment. In the first embodiment, the mark embedding portion determines a mark embedding position by using irradiation field data and through area data obtained by the extraction.recognition portion (image identification.extraction portion). In the second embodiment, a mark is embedded by using position information given by a mark position editing means.

When an operator presses a photo-taking parameter change key 123 shown in FIG. 2, he or she can call the photo-taking parameter change window as shown in FIG. 7. A sensor detection range 137 corresponds to the detection range (430×430 mm) of the standing position sensor panel 104. When the operator designates a printer and a film size, the image cut-out region 138 is displayed in the sensor detection range. The operator presses the mark layout key 140 to set the edit mode and places a mark X, or the cursor 139, in a desired position. To change the property of the mark, the operator presses the corresponding property key to set the property. The set mark is embedded in a photo-taken image. The mark is always displayed in a predetermined position during diagnosis and hence easy to see.

As described above, the X-ray photo-taking system according to the second embodiment of the present invention comprises the X-ray photo-taking system operation.display portion 108 for inputting and displaying photo-taking conditions, photo-taking parameters, object information, and photo-taking information, the information capture portion 1 for symbolizing the direction of an object to be examined during photo-taking, the photo-taking direction, the position of a photo-taking region, and the photo-taking attitude, the mark embedding portions 9 to 11 for embedding marks in a portion of an X-ray photo-taken image, the display control portion 2 for displaying, on the X-ray photo-taking system operation.display portion 108, an image in which a mark is embedded by the mark embedding portion 9 in an area where no photo-taking object is present within the range of an X-ray irradiation field, and for laterally inverting the image in accordance with the mark, and the transmission portion 12 for destination A and the transmission portion 13 for destination B which transmit an image in which marks are embedded by the mark embedding portions 10 and 11 onto the network 110. Accordingly, the system achieves the following functions and effects.

In the above arrangement, when an operator inputs photo-taking conditions, photo-taking parameters, object information, and photo-taking information via the X-ray photo-taking system operation.display portion 108, the information input portion 113, or the network 110, the mark embedding portions 9 to 11 embed, as marks, the direction of an object to be examined during photo-taking, the photo-taking direction, the position of a photo-taking region, and the photo-taking attitude in a predetermined position in a portion of an X-ray photo-taken image. The X-ray photo-taken image in which these marks are embedded is displayed on the X-ray photo-taking system operation.display portion 108 via the display control portion 2. Alternatively, the X-ray photo-taken image in which these marks are embedded is output to the film imager 111 or the image server 112 on the network 110 via the transmission portion 12 for destination A or the transmission portion 13 for destination B. Also, only by designating a photo-taking region, it is possible to set the direction of an object to be examined during photo-taking, the photo-taking direction, the position of a photo-taking region, and the photo-taking attitude, each of which is previously related to the photo-taking region. Free layout of the position of marking is also feasible.

Accordingly, by displaying an acquired X-ray photo-taken image on a display medium by attaching a mark, indicative of the photo-taking direction or photo-taking method, the photo-taking attitude of an object to be examined, or the position of a photo-taking region of the object, to a portion of the X-ray image, an operator can recognize the position (left, right, or center) of the photo-taking region of the object, the X-ray irradiation direction, or the photo-taking attitude only by seeing the X-ray image.

Additionally, pieces of information pertaining to the position of a photo-taking region of an object to be examined, X-ray irradiation direction, and photo-taking attitude are conventionally displayed in the form of a text in the same space as for photo-taking information and patient information. This makes the text display portion difficult to see. However, in the present invention, these pieces of information are easy to see because the text information can be narrowed down to the patient information and the photo-taking information.

Furthermore, when a doctor diagnoses a patient on the basis of an X-ray photo-taken image, a mark is always added to a predetermined position on the X-ray photo-taken image. This obviates the need to extract a portion easy to see or a through portion.

THIRD EMBODIMENT

Figure 8:
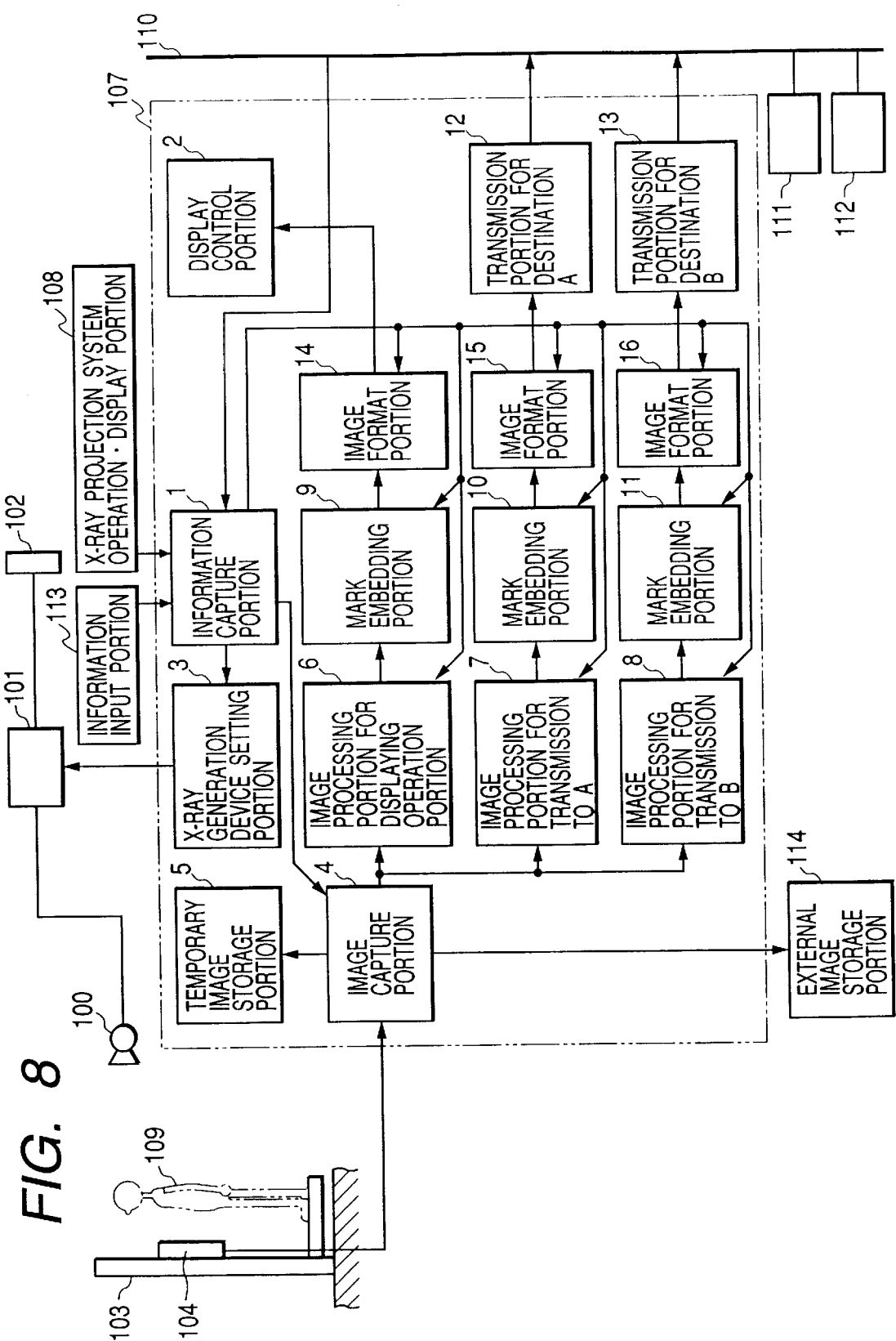
FIG. 8 is a block diagram showing the overall arrangement of an X-ray photo-taking system according to the third embodiment of the present invention.

FIG. 8 is a block diagram showing the overall arrangement of an X-ray photo-taking system according to the third embodiment of the present invention.

This X-ray photo-taking system according to the third embodiment of the present invention comprises an X-ray tube 100, an X-ray generation device control portion 101, an X-ray generation device operation.display portion 102, a standing position sensor unit 103, a standing position sensor panel 104, an X-ray photo-taking system control portion 107, an X-ray photo-taking system operation.display portion 108, a network 110, a film imager 111, an image server 112, an information input portion 113, and an external image storage portion 114. The X-ray photo-taking system control portion 107 includes an information capture portion 1, a display control portion 2, an X-ray generation device setting portion 3, an image capture portion 4, a temporary image storage portion 5, an image processing portion 6 for displaying operation portion, an image processing portion 7 for transmission to A, an image processing portion 8 for transmission to B, mark embedding portions 9, 10, and 11, a transmission portion 12 for destination A, a transmission portion 13 for destination B, and image format portions 14, 15, and 16.

This third embodiment of the present invention is the same as the above first and second embodiments except that the image format portions 14, 15, and 16 are added to the X-ray photo-taking system control portion 107. When photo-taking of an object to be examined is completed, the image format portions 14, 15, and 16 display the image in a predetermined format by looking up a format table (FIG. 10) that is classified in units of photo-taking regions and is preset. Note that the same reference numerals as in FIG. 1 denote parts having the same functions in FIG. 8, and a detailed description thereof will be omitted.

The characteristic feature of this third embodiment of the present invention is as follows. That is, when photo-taking of the same photo-taking region of one object to be examined is performed a plurality of times as in the case of "chast part front photo-taking and thoracic part side photo-taking, image reading is facilitated by displaying the photo-taken images of the same region at once, and it is desirable to reduce the number of films if films are used. For these reasons, separate images are simultaneously displayed on one film or monitor. The third embodiment of the present invention is characterized in that the layout of these photo-taken images can be automatically determined by the combination of set marks.

For example, in the case of "chast part back→front" and "chast part side right left". X-ray images of "chast part back→front" and "chast part side right→left" are customarily arranged on the right and the left, respectively, in accordance with trigonometry. In the case of "chast part back→front" and "chast part side left→right", however, an X-ray image of "chast part back→front" is arranged on the left and an X-ray image of "thoracic part side left→right" is arranged on the right in many instances.

Figure 9:
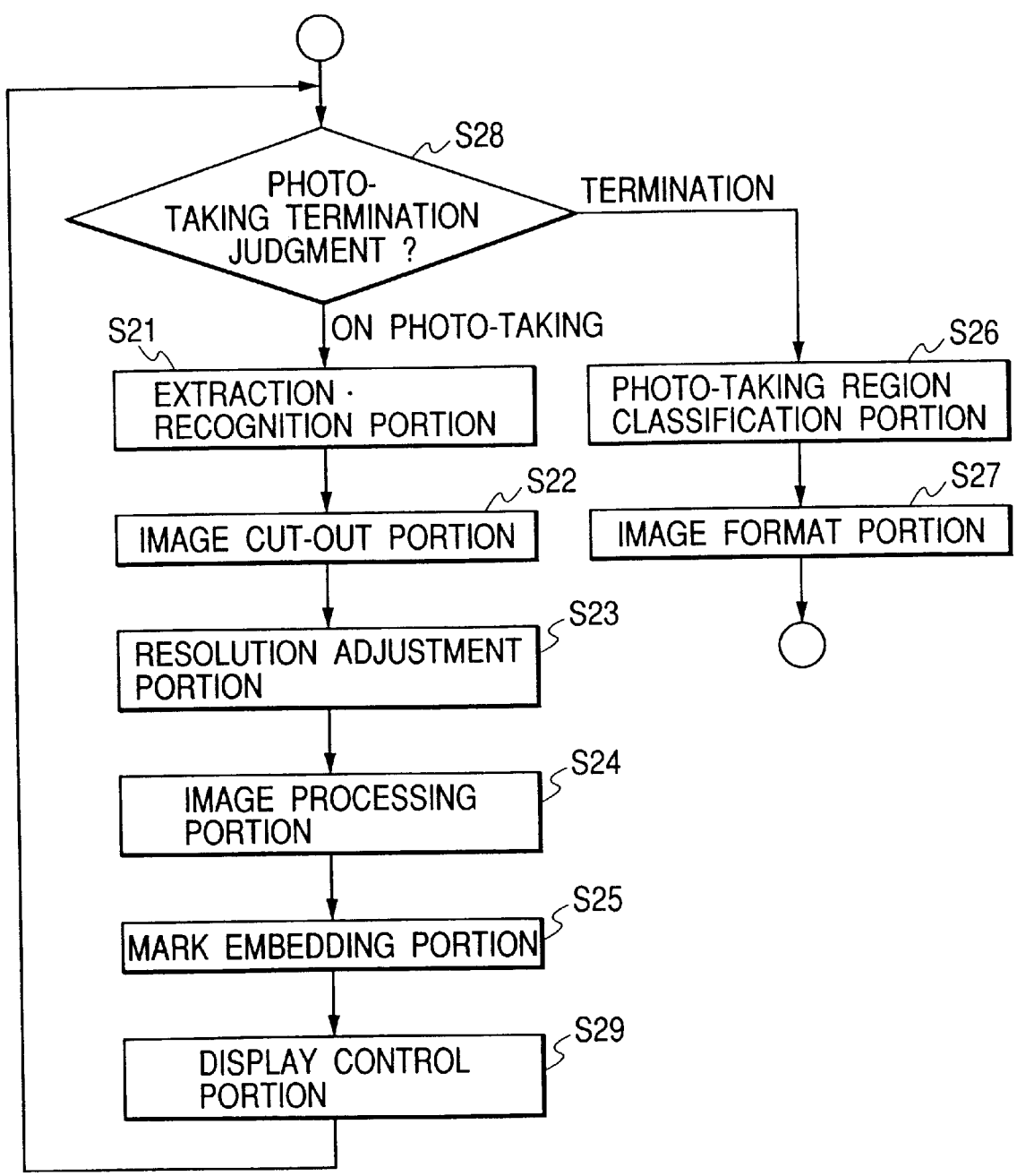
FIG. 9 is a flow chart of image processing in the X-ray photo-taking system according to the third embodiment of the present invention.

FIG. 9 is a flow chart of image processing in the X-ray photo-taking system according to the third embodiment of the present invention.

This flow chart is executed by the X-ray photo-taking system control portion 107. In step S28, a photo-taking termination judgement portion judges whether a plurality of photo-taking operations for a certain object to be examined are terminated. If photo-taking is being performed, processes in steps S21 to S25 are performed. In step S29, a display control portion displays the images. If photo-taking is terminated, the flow advances to step S26, and a photo-taking region classification portion classifies the images in units of photo-taking regions. In step S27, a photo-taken image format portion formats a plurality of X-ray images.

Figure 11:
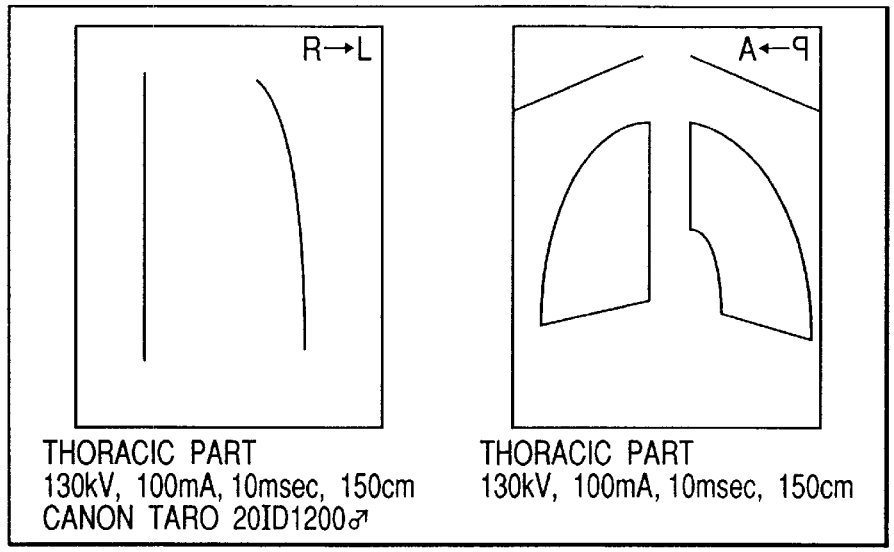
FIG. 11 is a view for explaining a format example in the X-ray photo-taking system according to the third embodiment of the present invention.
Figure 13:
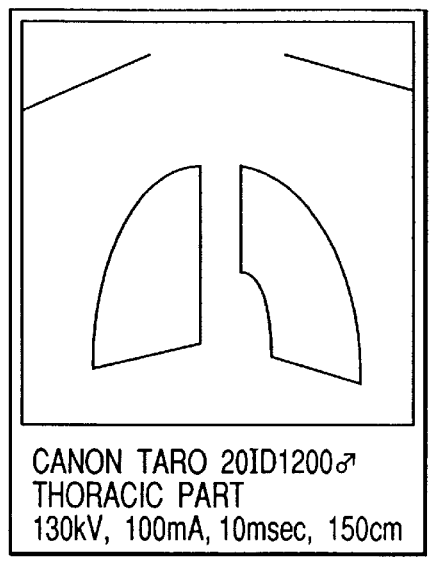
FIG. 13 is a view for explaining an image display method according to prior art.

FIG. 10 is a view for explaining the format table in the X-ray photo-taking system according to the third embodiment of the present invention. This format table defines formats in accordance with photo-taking directions and the positions of regions and can be changed by a setting key. In the format table shown in FIG. 10, combinations of photo-taking regions (chast part, wrist joint, . . . ) and marks (P→A, A→P, . . . ) indicating photo-taking directions are related to formats. For "thoracic part P→A" and "thoracic part R→L" at the top of FIG. 10, a format is as shown in FIG. 11.

Next, the operation of the X-ray photo-taking system according to the third embodiment of the present invention constructed as above will be described below.

A photo-taking procedure is performed in the same manner as in the first embodiment. Since a plurality of images are taken for one object to be examined, when the first photo-taking is completed, an operator selects the second photo-taking region by a photo-taking region select key 125 and performs photo-taking, without pressing a photo-taking termination key 126. The third and subsequent photo-taking operations are similarly performed. When all photo-taking operations are completed, the operator presses the photo-taking termination key 126.

When all photo-taking operations are completed and the photo-taking termination key 126 is pressed, the photo-taking termination judgement portion judges in step S28 of FIG. 9 that photo-taking is terminated and transfers the process to the photo-taking region classification portion in step S26. The photo-taking region classification portion in step S26 classifies the photo-taken X-ray images in units of photo-taking regions. On the basis of this classification, the photo-taken image format portion in step S27 transmits the photo-taken images to a printer or a storage so that the images are displayed in desired format. This is done by looking up the format table as shown in FIG. 10. In this way, images can be displayed in formats readily interpretable by a doctor.

As described above, the X-ray photo-taking system according to the third embodiment of the present invention comprises the X-ray photo-taking system operation.display portion 108 for inputting and displaying photo-taking conditions, photo-taking parameters, object information, and photo-taking information, the information capture portion 1 for symbolizing the direction of an object to be examined during photo-taking, the photo-taking direction, the position of a photo-taking region, and the photo-taking attitude, the mark embedding portions 9 to 11 for embedding marks in a portion of an X-ray photo-taken image, the display control portion 2 for displaying, on the X-ray photo-taking system operation.display portion 108, an image in which a mark is embedded by the mark embedding portion 9 in an area where no photo-taking object is present within the range of an X-ray irradiation field, and for laterally inverting the image in accordance with the mark, the transmission portion 12 for destination A and the transmission portion 13 for destination B which transmit an image in which marks are embedded by the mark embedding portions 10 and 11 onto the network 110, and the image format portions 14 to 16 for performing formatting on the basis of the format table such that a plurality of X-ray photo-taken images are displayed in predetermined format on the same display medium. Accordingly, the system achieves the following functions and effects.

In the above arrangement, when an operator inputs photo-taking conditions, photo-taking parameters, object information, and photo-taking information via the X-ray photo-taking system operation.display portion 108, the information input portion 113, or the network 110, the mark embedding portions 9 to 11 embed, as marks, the direction of an object to be examined during photo-taking, the photo-taking direction, the position of a photo-taking region, and the photo-taking attitude in a predetermined position in a portion of an X-ray photo-taken image. When X-ray phototaking of the object is completed, the image format portions 14 to 16 classify a plurality of X-ray photo-taken images in units of photo-taking regions and perform formatting such that these images are displayed in a predetermined format on the same display medium. The X-ray photo-taken image in which the marks are embedded is displayed on the X-ray photo-taking system operation.display portion 108 via the display control portion 2. Alternatively, the X-ray photo-taken image in which these marks are embedded is output to the film imager 111 or the image server 112 on the network 110 via the transmission portion 12 for destination A or the transmission portion 13 for destination B. Also, by designating only a photo-taking region, it is possible to set the direction of an object to be examined during photo-taking, the photo-taking direction, the position of a photo-taking region, and the photo-taking attitude, each of which is previously related to the photo-taking region.

Accordingly, by displaying an acquired X-ray photo-taken image on a display medium by attaching a mark, indicative of the photo-taking direction or photo-taking method, the photo-taking attitude of an object to be examined, or the position of a photo-taking region of the object, to a portion of the X-ray image, an operator can recognize the position (left, right, or center) of the photo-taking region of the object, the X-ray irradiation direction, or the photo-taking attitude only by seeing the X-ray image.

Additionally, pieces of information pertaining to the position of a photo-taking region of an object to be examined, X-ray irradiation direction, and photo-taking attitude are conventionally displayed in the form of a text in the same space as for photo-taking information and patient information. This makes the text display portion difficult to see. However, in the present invention, these pieces of information are easy to see because the text information can be narrowed down to the patient information and the photo-taking information.

Furthermore, when images of the same region but in different photo-taking directions are to be displayed on the same medium, formatting is performed on the basis of a mark indicating the photo-taking direction or the photo-taking method, the photo-taking attitude of an object to be examined, or the position of the region of the object. Therefore, formatting that is easy to see (readily interpretable by a doctor) can be performed with a simple operation.

The present invention can be applied to a system constituted by a plurality of devices or to an apparatus comprising a single device. Further, the object of the present invention can also be achieved by providing a storage medium storing program codes of software for performing the aforesaid functions according to the embodiments to a system or an apparatus, reading the program codes with a computer (e.g., CPU or MPU) of the system or apparatus from the storage medium, and then executing the program.

In this case, the program codes read from the storage medium realize the functions according to the embodiments, and the storage medium storing the program codes constitutes the invention.

As the storage medium for providing the program codes, it is possible to use, e.g., a floppy disk, a hard disk, an optical disk, a magnetooptical disk, CD-ROM, CD-R, a magnetic tape, a nonvolatile type memory card, and ROM.

Furthermore, besides aforesaid functions according to the above embodiments are realized by executing the program codes which are read by a computer, the present invention includes a case where an OS or the like working on the computer performs a part or entire processes in accordance with designations of the program codes and realizes functions according to the above embodiments.

Moreover, the present invention also includes a case where, after the program codes read from the storage medium are written in a function extension board which is inserted into the computer or in a memory provided in a function extension unit which is connected to the computer, CPU or the like contained in the function extension board or unit performs a part or entire process in accordance with designations of the program codes and realizes functions of the above embodiments.

In the X-ray photo-taking system, as has been described above, by displaying an acquired X-ray photo-taken image on a display medium by attaching a mark, indicative of the photo-taking direction or photo-taking method, the photo-taking attitude of an object to be examined, or the position of a photo-taking region of the object, to a portion of the X-ray image, an operator can recognize the position (left, right, or center) of the photo-taking region of the object, the X-ray irradiation direction, or the photo-taking attitude only by seeing the X-ray image. Also, pieces of information pertaining to the position of a photo-taking region of an object to be examined, X-ray irradiation direction, and photo-taking attitude are conventionally displayed in the form of a text in the same space as for photo-taking information and patient information. This makes the text display portion difficult to see. However, in the present invention, these pieces of information are easy to see because the text information can be narrowed down to the patient information and the photo-taking information.

Additionally, whether a symbol is to be inverted or not is determined for each item (photo-taking region or photo-taking direction). Therefore, a symbol can be displayed by inverting it, or without inverting it, for each item (photo-taking region or photo-taking direction) in accordance with a doctor's or hospital's demand.

Furthermore, a symbol is embedded in a desired form in a set position of an X-ray photo-taken image. Hence, when a doctor diagnoses a patient on the basis of an X-ray photo-taken image, a symbol is always added to a predetermined position on the x-ray photo-taken image. This obviates the need to extract a portion easy to see or a through portion.

Also, an image is laterally inverted such that the heart is positioned on the right-hand side, so a doctor need not take the trouble to invert the image. Since the photo-taking direction is displayed in an image area, the irradiation direction of X-rays is known at a glance. Even when a radiologist laterally inverts an image, marks are inverted simultaneously with the image, so the direction of photo-taking is known at a look.

Additionally, when images of the same region but in different photo-taking directions are to be displayed on the same medium, formatting is performed on the basis of a mark indicating the photo-taking direction or the photo-taking method, the photo-taking attitude of an object to be examined, or the position of the region of the object. Therefore, formatting that is easy to see can be performed with a simple operation.

What is claimed is:

1. A radiographic apparatus for acquiring a radiograph of an object to be examined, comprising:
    symbolizing means for symbolizing information pertaining to radiography of the object; and
    symbol embedding means for embedding a symbol obtained by said symbolizing means in a portion of the radiograph,
    wherein said symbol embedding means inverts the symbol obtained by said symbolizing means in accordance with at least one of input information and set information.

2. An apparatus according to claim 1, further comprising:
    information input means for inputting at least one of radiographic conditions, image processing parameters, object information for identifying the object, and a region of the object to be radiographed.

3. An apparatus according to claim 1, wherein said symbol embedding means inverts the symbol laterally and embeds a laterally inverted symbol.

4. An apparatus according to claim 1, wherein the symbol obtained by said symbolizing means represents at least one of a radiographing direction relative to the object, an attitude of the object, and a region of the object to be radiographed.

5. An apparatus according to claim 1, further comprising:
    selecting means for selecting a radiographing mode; and
    relating means for relating the symbol to be obtained by said symbolizing means to the mode selected by said selecting means,
    wherein said symbolizing means symbolizes the information on the basis of the mode selected by said selecting means and the relation related by said relating means.

6. An apparatus according to claim 1, further comprising:
    image inverting means for inverting the radiograph in accordance with at least one of input information and set information.

7. An apparatus according to claim 6, wherein said symbol embedding means inverts the symbol obtained by said symbolizing means in accordance with the inversion of the radiograph by said image inverting means.

8. An apparatus according to claim 1, further comprising:
    image formatting means for performing formatting such that a plurality of radiographs, in each of which a symbol is embedded by said symbol embedding means, are laid out in a predetermined format.

9. An apparatus according to claim 1, wherein a symbol embedding means is provided for each type of output medium.

10. An apparatus according to claim 1, further comprising:
    image transmitting means for transmitting a radiograph in which the symbol has been embedded to image output means or an image server.

11. An apparatus according to claim 10, wherein the image output means or the image server is connected via a network.

12. An apparatus according to claim 1, wherein the information pertaining to radiography of the object can be input by at least one of reading a magnetic card, reading a bar code, receiving the information via a network linked to a hospital information system, and receiving the information via an operation portion.

13. An apparatus according to claim 1, wherein the input information or the set information includes at lease one of a region of the object to be radiographed, a radiographing direction relative to the object, and independently input or preset inversion/non-inversion selection information.

14. A radiographic apparatus for acquiring a radiograph of an object to be examined, comprising:
   symbolizing means for symbolizing information pertaining to radiography of the object;
   symbol embedding means for embedding a symbol obtained by said symbolizing means in a portion of the radiograph; and
   inversion/non-inversion determining means for determining whether the symbol obtained by said symbolizing means is to be inverted or not, in accordance with at least one of input information and set information.

15. An apparatus according to claim 14, wherein the input information or the set information includes at least one of a region of the object to be radiographed, a radiographing direction relative to the object, and independently input or preset inversion/non-inversion selection information.

16. A radiographic apparatus for acquiring a radiograph of an object to be examined, comprising:
   symbolizing means for symbolizing information pertaining to radiography of the object;
   symbol embedding means for embedding a symbol obtained by said symbolizing means in a portion of the radiograph;
   first extracting means for extracting an irradiation field of the radiograph; and
   second extracting means for extracting a through region of the radiograph which is where no object exists within a region of the irradiation field,
   wherein said symbol embedding means embeds the symbol obtained by said symbolizing means in the through region.

17. A radiographic apparatus for acquiring a radiograph of an object to be examined, comprising:
   symbolizing means for symbolizing information pertaining to radiography of the object;
   symbol embedding means for embedding a symbol obtained by said symbolizing means in a portion of the radiograph; and
   embedding setting means for setting at least one of a position where the symbol is to be embedded in the radiograph, a shape and size of the symbol, and for determining whether the symbol is to be inverted or not,
   wherein said symbol embedding means embeds the symbol based on information set or determined by said embedding setting means.

18. An apparatus according to claim 17, further comprising:
   embedding changing means for changing the information set or as determined by said embedding setting means.

19. A radiographic apparatus for acquiring a radiograph of an object to be examined, comprising:
   symbolizing means for symbolizing information pertaining to radiography of the object, wherein a symbol obtained by said symbolizing means represents at least one of a radiographic direction relative to the object, an attitude of the object, and a region of the object to be radiographed;
   symbol embedding means for embedding the symbol obtained by said symbolizing means in a portion of the radiograph; and
   image formatting means for performing formatting such that a plurality of radiographs, in each of which a symbol is embedded by said symbol embedding means, are laid out in a format in accordance with a combination of symbols to be embedded by said symbol embedding means.

20. An image taking apparatus for acquiring an image of an object to be examined, comprising:
   symbolizing means for symbolizing information pertaining to image taking of the object; and
   symbol embedding means for embedding a symbol obtained by said symbolizing means in a portion of the image,
   wherein said symbol embedding means inverts the symbol obtained by said symbolizing means in accordance with at least one of input information and set information.

21. A method applied to a radiographic apparatus for acquiring a radiographic image of an object to be examined, comprising:
   a symbolizing step of symbolizing information pertaining to radiography of the object; and
   a symbol embedding step of embedding a symbol obtained in said symbolizing step in a portion of the radiographic image,
   wherein, in said symbol embedding step, the symbol obtained in said symbolizing step is inverted in accordance with at least one of input information and set information.

22. A method according to claim 21 further comprising:
   an information input step of inputting at least one of radiographic conditions, image processing parameters, object information for identifying the object, and a region of the object to be radiographed.

23. A method according to claim 21, wherein said symbol embedding step comprises inverting the symbol laterally and embedding a laterally inverted symbol.

24. A method according to claim 21, wherein the symbol obtained in said symbolizing step represents at least one of a radiographing direction relative to the object, an attitude of the object, and a region of the object to be radiographed.

25. A method according to claim 21, further comprising:
   a selecting step of selecting a radiographing mode; and
   a relating step of relating the symbol to be obtained in said symbolizing step to the mode selected in said selecting step,
   wherein, in said symbolizing step, the information is symbolized on the basis of the mode selected in said selecting step and the relation related in said relating step.

26. A method according to claim 21, further comprising:
   an image inverting step of inverting the radiograph in accordance with input information or set information.

27. A method according to claim 26, wherein the symbol embedding step comprises inverting the symbol obtained in said symbolizing step in accordance with the inversion of the radiograph in said image inverting step.

28. A method according to claim 21, further comprising:
   an image formatting step of performing formatting such that a plurality of radiographs, in each of which a symbol is embedded in said symbol embedding step, are laid out in a predetermined format on the same display medium.

29. A method according to claim 21, wherein the symbol embedding step is provided for each type of output medium.

30. A method according to claim 21, further comprising:
   an image transmission step of transmitting a radiograph in which the symbol has been embedded to image output means or an image server.

31. A method according to claim 30, wherein the image output means or the image server is connected via a network.

32. A method according to claim 21, wherein the information pertaining to radiography of the object can be input by at least one of reading a magnetic card, reading a bar code, receiving the information via a network linked to a hospital information system, and receiving the information via an operation portion.

33. A method of acquiring a radiograph of an object to be examined, comprising:

a symbolizing step of symbolizing information pertaining to the radiography of the object;

an embedding step of embedding a symbol obtained in said symbolizing step in a portion of the radiograph; and an inversion/non-inversion determination step of determining whether the symbol obtained in said symbolizing step is to be inverted or not, in accordance with at least one of input information and set information.

34. A method of acquiring a radiograph of an object to be examined, comprising:

a symbolizing step of symbolizing information pertaining to radiography of the object;

a symbol embedding step of embedding a symbol obtained in said symbolizing step in a portion of the radiograph;

a first extraction step of extracting an irradiation field of the radiograph; and a second extraction step of extracting a through region of the radiograph which is where no object exists within a region of the irradiation field, wherein the symbol embedding step comprises embedding the symbol obtained in said symbolizing step in the through region.

35. A method of acquiring a radiograph of an object to be examined, comprising:

a symbolizing step of symbolizing information pertaining to radiography of the object;

a symbol embedding step of embedding a symbol obtained in said symbolizing step in a portion of the radiograph; and an embedding setting step of setting at least one of a position where the symbol is to be embedded in the radiograph, a shape and size of the symbol, and for determining whether the symbol is to be inverted or not, wherein said symbol embedding step comprises embedding the symbol based on information set or determined in said embedding setting step.

36. A method according to claim 35, further comprising: an embedding changing step of changing the information set or as determined in said embedding setting step.

37. A method of acquiring a radiograph of an object to be examined, comprising:

a symbolizing step of symbolizing information pertaining to radiography of the object, wherein a symbol obtained in said symbolizing step represents at least one of a radiographing direction relative to the object, an attitude of the object, and a region of the object to be radiographed;

a symbol embedding step of embedding the symbol obtained in said symbolizing step in a portion of the radiograph; and an image formatting step of performing formatting such that a plurality of radiographs, in each of which a symbol is embedded in said symbol embedding step, are laid out in a format in accordance with a combination of symbols to be embedded in said symbol embedding step.

38. An image display method applied to an image taking system for acquiring an image of an object to be examined, comprising:

a symbolizing step of symbolizing information pertaining to image taking of the object, wherein a symbol obtained in said symbolizing step represents at least one of a radiographing direction relative to the object, an attitude of the object, and a region of the object to be radiographed; and a symbol embedding step of embedding a symbol obtained in said symbolizing step by embedding the symbol in a portion of the image, wherein, in said symbol embedding step, the symbol obtained in said symbolizing step is inverted in accordance with at least one input information and set information.

39. A computer-readable storage medium storing a program for executing a method applied to a radiographic apparatus for acquiring a radiograph of an object to be examined, the method comprising:

a symbolizing step of symbolizing information pertaining to radiography of the object; and a symbol embedding step of embedding a symbol obtained in said symbolizing step in a portion of the radiographic image, wherein, in said symbol embedding step, the symbol obtained in said symbolizing step is inverted in accordance with at least one of input information and set information.

40. A radiographic system for acquiring a radiograph of an object to be examined, the system comprising:

symbolizing means for symbolizing information pertaining to radiography of the object; and symbol embedding means for embedding a symbol obtained by said symbolizing means in a portion of the radiograph, wherein said symbol embedding means inverts the symbol obtained by said symbolizing means in accordance with at least one of input information and set information.

41. A radiographic system for acquiring a radiograph of an object to be examined, the system comprising:

symbolizing means for symbolizing information pertaining to radiography of the object;

symbol embedding means for embedding a symbol obtained by said symbolizing means in a portion of the radiograph; and inversion/non-inversion determining means for determining whether the symbol obtained by said symbolizing means is to be inverted or not, in accordance with at least one of input information and set information.

42. A radiographic system for acquiring a radiograph of an object to be examined, comprising:

symbolizing means for symbolizing information pertaining to radiography of the object;

symbol embedding means for embedding a symbol obtained by said symbolizing means in a portion of the radiograph;

first extracting means for extracting an irradiation field of the radiograph; and second extracting means for extracting a through region of the radiograph which is where no object exists within a region of the irradiation field, wherein said symbol embedding means embeds the symbol obtained by said symbolizing means in the through region.

43. A radiographic system for acquiring a radiograph of an object to be examined, comprising:

symbolizing means for symbolizing information pertaining to radiography of the object;

symbol embedding means for embedding a symbol obtained by said symbolizing means in a portion of the radiograph; and embedding setting means for setting at least one of a position where the symbol is to be embedded in the radiograph, a shape and a size of the symbol, and for determining whether the symbol is to be inverted or not, wherein said symbol embedding means embeds the symbol based on information set or determined by said embedding setting means.

44. A radiographic system for acquiring a radiograph of an object to be examined, comprising:

symbolizing means for symbolizing information pertaining to radiography of the object, wherein a symbol obtained by said symbolizing means represents at least one of a radiographing direction relative to the object, an attitude of the object, and a region of the object to be radiographed;

symbol embedding means for embedding the symbol obtained by said symbolizing means in a portion of the radiograph; and image formatting means for performing formatting such that a plurality of radiographs, in each of which a symbol is embedded by said symbol embedding means, are laid out in a format in accordance with a combination of symbols to be embedded by said symbol embedding means.

45. An image taking system for acquiring an image of an object to be examined, comprising:

symbolizing means for symbolizing information pertaining to image taking of the object; and symbol embedding means for embedding a symbol obtained by said symbolizing means by embedding the symbol in a portion of the image, wherein said symbol embedding means inverts the symbol obtained by said symbolizing means in accordance with at least one of input information and set information.

\* \* \* \* \*

UNITED STATES PATENT AND TRADEMARK OFFICE
CERTIFICATE OF CORRECTION

PATENT NO. : 6,542,579 B1
DATED : April 1, 2003
INVENTOR(S) : Toru Takasawa

It is certified that error appears in the above-identified patent and that said Letters Patent is hereby corrected as shown below:

<u>Title page,</u>
Item [*] Notice, should read: -- This patent issued on a continued prosecution application filed under 37 CFR 1.53(d). and is subject to the twenty year patent term provisions of 35 U.S.C. 154(a)(2). --
Insert Item: -- [74] *Attorney, Agent, or Firm*-Fitzpatrick, Cella, Harper & Scinto -- after "* cited by Examiner" and before "*Primary Examiner…*".

<u>Column 2,</u>
Line 26, "chast" should read -- chest --.

<u>Column 3,</u>
Line 59, "chast" should read -- chest --; and
Line 61, "(back e front" should read -- (back→front --.

<u>Column 4,</u>
Line 15, "chast" should read -- chest --.

<u>Column 7,</u>
Line 19, "UGA" should read -- VGA --.

<u>Column 8,</u>
Line 17, "chast" should read -- chest --; and
Lines 53 and 66, "thoracic" should read -- chest --.

<u>Column 9,</u>
Line 1, "thoracic" should read -- chest --; and
Lines 3, 4 and 56, "chast" should read -- chest --.

<u>Column 11,</u>
Line 3, "chast" should read -- chest --; and
Line 63, "Po" should read -- P→ --.

<u>Column 12,</u>
Line 10, "chast" should read -- chest --.

<u>Column 16,</u>
Lines 34 and 44, "chast" should read -- chest --;
Line 45, "left"." should read -- left", --;
Line 45, ""chast" should read -- "chest -- (both occurrences);
Lines 46, 48, 49 and 50, ""chast" should read -- "chest --; and
Line 51, ""thoracic" should read -- "chest --.

UNITED STATES PATENT AND TRADEMARK OFFICE
CERTIFICATE OF CORRECTION

PATENT NO. : 6,542,579 B1
DATED : April 1, 2003
INVENTOR(S) : Toru Takasawa

It is certified that error appears in the above-identified patent and that said Letters Patent is hereby corrected as shown below:

Column 17,
Line 7, "(chast" should read -- (chest --.

Signed and Sealed this

Twentieth Day of January, 2004

JON W. DUDAS
*Acting Director of the United States Patent and Trademark Office*